United States Patent [19]

Teraoka et al.

[11] Patent Number: 5,587,082
[45] Date of Patent: Dec. 24, 1996

[54] HIGH OSMOTIC PRESSURE CHROMATOGRAPHY

[76] Inventors: Iwao Teraoka, 73 Batavia Pl., Harrison, N.Y. 10528; Min Luo, 229 W. 62nd St., New York, N.Y. 10023

[21] Appl. No.: 480,238

[22] Filed: Jun. 7, 1995

[51] Int. Cl.$^6$ ................................................. B01D 15/08
[52] U.S. Cl. ........................ 210/635; 210/656; 210/198.2
[58] Field of Search ............................. 210/635, 656, 210/659, 198.2; 436/161; 528/482

[56] References Cited

U.S. PATENT DOCUMENTS

| | | | |
|---|---|---|---|
| 3,855,129 | 12/1974 | Abrahams et al. | 210/198.2 |
| 3,869,409 | 3/1975 | Bebris et al. | 210/656 |
| 3,873,514 | 3/1975 | Chu et al. | 210/635 |
| 4,366,060 | 12/1982 | Leiser et al. | 210/635 |
| 4,422,942 | 12/1983 | Allington | 210/659 |
| 4,426,292 | 1/1984 | Wernick et al. | 210/635 |
| 4,915,843 | 4/1990 | Taniguchi et al. | 210/635 |
| 5,019,270 | 5/1991 | Afeyan et al. | 210/656 |
| 5,057,296 | 10/1991 | Beck | 423/277 |
| 5,089,126 | 2/1992 | Silebi | 210/198.2 |
| 5,108,725 | 4/1992 | Beck et al. | 423/263 |
| 5,133,868 | 7/1992 | Atwood | 210/656 |
| 5,160,625 | 11/1992 | Jönsson et al. | 210/635 |
| 5,183,604 | 2/1993 | Langhorst | 264/40.1 |
| 5,228,989 | 7/1993 | Afeyan et al. | 210/198.2 |
| 5,372,721 | 12/1994 | Langhorst | 210/635 |
| 5,384,042 | 1/1995 | Afeyan et al. | 210/198.2 |

OTHER PUBLICATIONS

Felix Franks, "Protein Biotechnology, Isolation, Characterization, and Stabilization" (1993) pp. 67–69, 549–557 and 563–572.

Iwao Teraoka, A. Dube, 1994 Mar. Meeting "Interferometric Study of Concentration Equilibria of Polystyrene Solutions with a Porous Glass Bead", Abstract.

American Polymer Standards Corporation, Polymer Standards Catalog, Jun. 1, 1993, pp. 1–21, and 24–44.

Richard E. Boehm, Daniel E. Martire, Daniel W. Armstrong, Khanh H. Bui, "Theory of Homopolymer Retention in Semidilute Solutions Using Liquid Chromatography", Macromolecules vol. 17, No. 3, 1984, pp. 400–407.

Iwao Teraoka, Ziming Zhou, Kenneth H. Langley, Frank E. Karasz, "Partitioning Inversion of a Bimodal Polymer Solution in Confined Geometrics", Macromolecules, vol. 26, No. 12, 1993, pp. 3223–3226.

Iwao Teraoka, Kenneth H. Langley, Frank E. Karasz, "Diffusion of Polystyrene in Controlled Pore Glasses: Transition from the Dilute to the Semidilute Regime", Macromolecules vol. 26, No. 2, 1993, pp. 287–297.

Pressure Chemical Co., Product Information, "Polymer Standards and Instrument Calibrants", pp. 1–10. undated.

Scientific Polymer Products, Inc., Product Information, "Analytical Polymer Standards", pp. 9–13. undated.

(List continued on next page.)

*Primary Examiner*—Ernest G. Therkorn
*Attorney, Agent, or Firm*—Cushman Darby & Cushman IP Group of Pillsbury Madison & Sutro, LLP

[57] ABSTRACT

New separation methods termed Enhanced Partitioning Fractionation (EPF) and High Osmotic Pressure Chromatography (HOPC) are described. The HOPC method involves passing large amounts of concentrated polymer solutions over porous material in a packed column. The concentration is high enough to allow for polymer chain overlap and to generate high osmotic pressures with respect to the porous material. The resulting high osmotic pressure causes increased separation of the polymer sample based on molecular size. The higher molecular weight components are concentrated in the initial fractions of eluent collected, whereas lower molecular weight components are concentrated in later fractions. The molecular weight of each fraction decreases with each successive fraction of eluent. The method is applicable to a wide variety of polymers and provides significant performance advantages to conventional preparative scale GPC. EPF is not a chromatographic procedure, but allows for fractionation of concentrated polymer solutions that generate high osmotic pressures in contact with porous material.

21 Claims, 17 Drawing Sheets

OTHER PUBLICATIONS

Polymer Source, Inc. Product Information, "Hydrophobic Polymers; Hydrophilic Polymers", pp. 1–18. undated.

Polysciences, Inc., Polymer/Monomer Catalog, "Polymer Molecular Weight Standards", pp. 20–21. undated.

Juris L. Ekmanis, "Preparative Gel Permeation Chromatography", Waters Lab Highlights No. 068, 1985 Pittsburgh Conference, New Orleans, LA pp. 1–34.

Iwao Teraoka, Ziming Zhou, Kenneth H. Langley, Frank E. Karasz, "Molecular Weight–Sensitive Separation of a Bimodal Polymer Mixture Using Nanoscale Porous Materials", Macromolecules vol. 26, No. 22, 1993, pp. 6081–6084.

Mark, Bikales, Overberger, Menges, "Encyclopedia of Polymer Science and Engineering" Second Edition, vol. 3, 1985, pp. 501–548.

Fred W. Billmeyer, Jr., Chapter Seven, Polymer Solutions, Textbook of Polymer Science, Third Edition, 1994, pp. 151–185.

Iwao Teraoka, Anil Dube, Weak–to–Strong Penetration Transition and its Application to Fractionation of Polymers, Waters International GPC Symposium '94, Waters R. Nielson, Ed., 1994, pp. 547–557.

A. Dube, I. Teraoka, Enhanced Partitioning Fractionation of a Bimodal Mixture of Polystyrene Using Porous Glass Beads, Macromolecules, 28, 1995, pp. 2592–2594.

R. J. Tonucci, B. L. Justus, A. J. Campillo, C. E. Ford, Nanochannel Array Glass, Science, 30 Oct. 1992, vol. 258, pp. 783–785.

C. T. Kresgu, M. E. Leenowiez, W. J. Rath, J. C. Vartull, J. S. Beck, Ordered Mesoporous Molecular Sieves Synthesized by a Liquid–Crystal Template Mechanism, Nature, vol. 359, 22 Oct. 1992, pp. 710–712.

Richard H. Clarke, Compact Disk, McGraw–Hill Encyclopedia of Science & Technology, 7th Edition, pp. 213–215.

R. M. Pisipati, J. M. Newcome, H. M. Lower, A New Substrate for Portable Optical Discs, Plastics Engineering, Apr. 1995, pp. 33–36.

Polycarbonates, Encyclopedia of Polymer Science and Engineering, vol. 11, 1988, pp. 649–718.

Information Storage Materials, Ullmann's Encyclopedia of Industrial Chemistry, Fifth Edition, vol. A14, 1989, pp. 171–239.

5,587,082

HIGH OSMOTIC PRESSURE CHROMATOGRAPHY

BACKGROUND OF THE INVENTION

1. Field of the Invention

The invention relates to a chromatographic process, and in particular, high osmotic pressure chromatography in which large amounts of concentrated samples of polymer are separated based on molecular size with use of porous materials.

2. Description of Related Art

The separation of mixtures based on molecular size (or hydrodynamic volume) is a widely applicable, industrially important process. For example, separation based on molecular size is important in the polymer industry, where the molecular weight and the molecular weight distribution of samples must be ascertained, and samples of polymers having carefully controlled molecular weight and molecular weight distribution must be prepared. Separation based on molecular size is also crucial to the biotechnology industry in, for example, the purification of proteins.

Polymer samples having narrow molecular weight distributions are used for, among other things, the calibration of columns for gel permeation chromatography, GPC, also called size exclusion chromatography. The conventional GPC method is used to separate molecules based on hydrodynamic volume for both analytical and preparative purposes, although the serious disadvantages of preparative scale GPC prevent even more wide use of the technique. In addition to GPC, fractional precipitation is another process to separate macromolecular mixtures based on molecular size. Ultracentrifugation and field-flow fractionation are other methods in the art.

However, conventional physical separation techniques are well-known to be cumbersome, inefficient, and time-consuming, particularly after scaling up. All of the techniques consume a large amount of solvent which is often hazardous. Physical separation methods are better suited for analytical rather than preparative purposes. A long-felt need exists to increase the cost efficiency by which macromolecular mixtures can be separated based on molecular size.

In addition to their preparation by physical separation methods, polymer samples having narrow molecular weight distributions can also be prepared directly by anionic polymerization methods. However, anionic polymerization is limited because, for among other reasons, the solvent for polymerization must be inert under anionic polymerization conditions, and therefore, many polymers cannot be prepared by anionic methods.

In the conventional GPC method, a small amount of dilute solution of polymer having a relatively broad molecular weight distribution is introduced onto a chromatographic column packed with solvent-imbibed porous materials such as porous silica or crosslinked polymer gel, and the column is subsequently washed with pure solvent to elute the polymer sample. Polymer molecules are partitioned between the mobile phase (outside the pores) and the stationary phase (inside the pores) at every plate in the column as the mobile phase flows through the column. As the sample is transferred down the column by the mobile phase, the higher molecular weight components tend to move ahead of the lower molecular weight components. The distribution in molecular weight broadens the original narrow band of the injected solution. As a result, the higher molecular weight polymer molecules elute from the column before the lower molecular weight polymer molecules. However, there is a broadening in the sample band even for a perfectly monodisperse polymer sample (inherent broadening). Therefore, the bands for different molecular weight fractions can overlap considerably.

In conventional GPC, low concentrations of the polymer sample are imperative to allow each polymer molecule to interact independently with the pore. The presence of additional interactions between polymer chains at higher concentrations results in overlapping of bands and loss of resolution.

Hence, it is critical in conventional GPC that the concentration of injected sample be sufficiently lower than the overlap concentration, which is defined as the concentration at which polymer chains begin to overlap with neighboring chains in solution. The overlap concentration, $c^*$, as known to those skilled in the art, divides the dilute from the semi-dilute region for a polymer solution. Chromatographers are alert to "overloading" the column, which overloading reduces separation efficiency. Usually during scale-up, some overloading may be attempted to improve process yields, but such overloading is limited and exercised with caution at the expense of resolution and more careful fraction cutting.

In addition, conventional GPC practice dictates that the sample should be in as narrow a band as possible after the sample is introduced onto the column. The low efficiency of the conventional preparative GPC process can also be ascribed to the fact that, at any one point in time during the conventional GPC separation process, only those regions of the column at which the bands of the polymer sample are located are actively effecting the separation. In other words, at any one point of time, most of the column is not in contact with the sample and is not being used, which again limits the overall efficiency of the conventional GPC method.

These GPC problems are not easily surmounted. Previous attempts to overcome the low processing capacities such as the use of thicker and longer columns have found limited success. In addition, the inherent band broadening has made it difficult to separate further samples already having a narrow molecular weight distribution.

SUMMARY AND OBJECTS OF THE PRESENT INVENTION

Objects of the present invention include, among others, (i) improving the separation efficiency by which a wide variety of polymer products having narrow molecular weight distributions can be prepared, (ii) preparing polymer products that have molecular weight distributions more narrow than the distributions of state-of-the-art products, (iii) making polymer purification by chromatography more environmentally benign, and (iv) preparing useful articles from the polymer products.

These and other objects are achieved in the present invention by novel techniques called high osmotic pressure chromatography (HOPC) and enhanced partitioning fractionation (EPF).

HOPC has only superficial resemblance to conventional GPC. The HOPC method is based on physical principles not relevant to conventional GPC. In fact, the new HOPC method is anathema to conventional GPC practice.

The HOPC method involves providing a solution of polymer dissolved in a first solvent in which the polymer has an initial polydispersity index (PDI, the ratio of weight average to number average molecular weight) greater than 1.000 (or equivalently, absolute one) and includes higher and lower molecular weight polymer components. The polymer is dissolved in the first solvent at a concentration about equal to or greater than the overlap concentration, c*, of the polymer. However, the concentration is less than the concentration at which the polymer solution is no longer a fluid.

Then, the polymer solution is passed as a mobile phase through a chromatographic matrix to generate an eluent. The matrix includes a porous material imbibed with a second solvent which acts as a stationary phase in communication with the mobile phase. The porous material has pore openings of a dimension on the order of the molecular size of the polymer that allows the lower and higher molecular weight polymer components to migrate selectively between the mobile phase and the stationary phase to effect size-based partitioning of the polymer. This selective migration is enhanced by a relatively high osmotic pressure generated because the concentration is about equal to or greater than the overlap concentration c*. Finally, the polymer is eluted from the porous material.

An HOPC method also comprises the steps of providing a solution of polymer dissolved in a first solvent, the polymer having an initial polydispersity index greater than 1.000 and including higher and lower molecular weight polymer components. The polymer is dissolved in the first solvent at a concentration about equal to or greater than an overlap concentration, c*, of the polymer but less than a concentration at which the solution is no longer fluid. Next, the solution is passed as a mobile phase onto a porous chromatographic matrix imbibed with a second solvent acting as a stationary phase until at least 50% of the matrix is in contact with the solution. Finally, the mobile phase is eluted from the matrix.

The EPF method involves providing a first mixture including a polymer dissolved in a first solvent, in which the polymer has a polydispersity index (PDI) greater than 1.000 and includes higher and lower molecular weight polymer components. The polymer is dissolved in the first solvent at a concentration about equal to or greater than the overlap concentration, c*, of the polymer. However, the concentration is less than the concentration at which the mixture is no longer fluid. A next step involves contacting the first mixture with a porous material imbibed with a second solvent. The porous material has pore openings of a dimension on the order of a molecular size of the polymer that allows the lower molecular weight polymer components to migrate selectively from the first mixture to within the porous material to effect size-based partitioning of the polymer. A second mixture enriched in higher molecular weight components is formed outside of the porous material and the porous material is imbibed with a solution enriched in the lower molecular weight polymer components. A further step in EPF involves separating the second mixture enriched in higher molecular weight components from the porous material. If desired, the porous material can also, in a second stage of EPF, be washed with a third solvent that extracts the lower molecular weight components from the imbibed solution enriched in lower molecular weight components.

Advantages of the present invention include, among others, improved separation efficiencies, less environmental harm, and products of better purity (more narrow molecular weight distribution).

DETAILED DESCRIPTION OF THE PRESENT INVENTION

Figure 1:
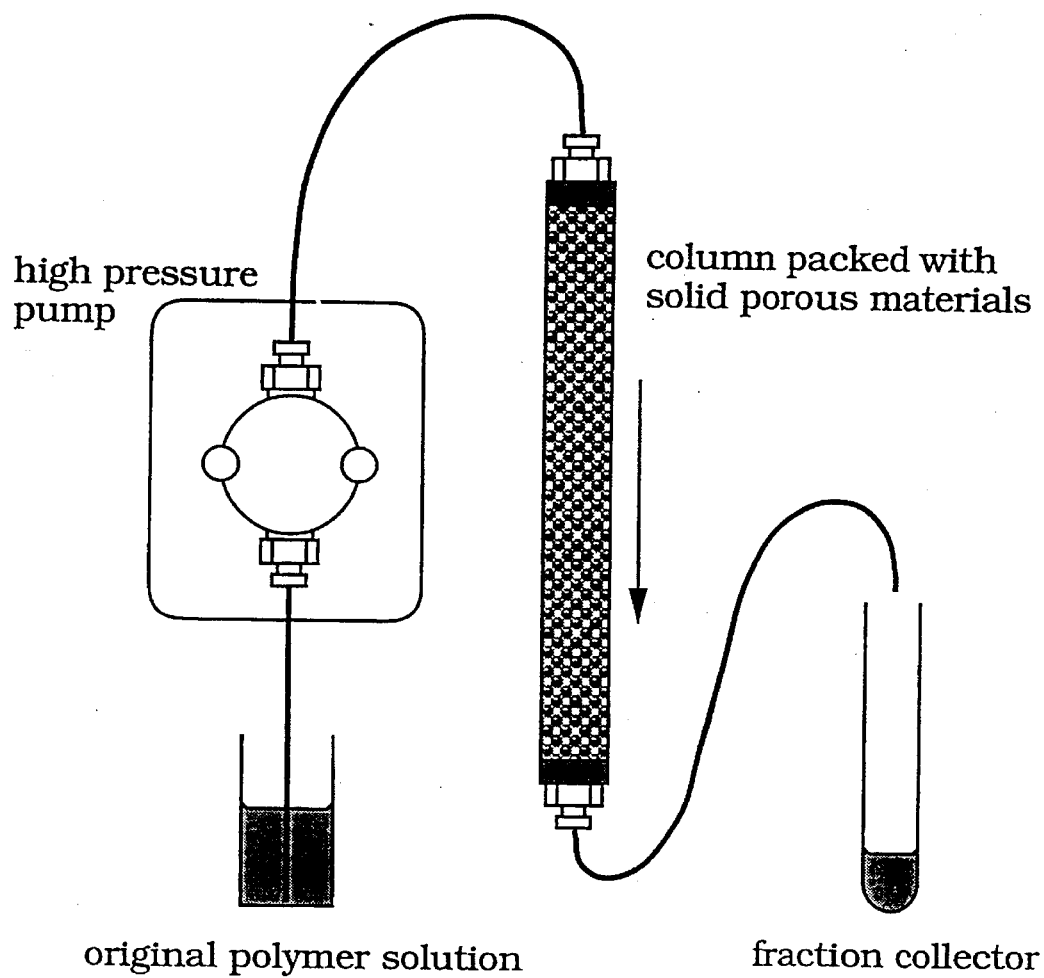
FIG. 1 illustrates an example of a chromatographic system for effecting HOPC.

The present invention involves a novel application of osmotic pressure to solve problems in separation. Discussion about osmotic pressure includes the following publications: Teraoka, I.; Langley, K. H.; and Karasz, F. E. *Macromolecules* 26,287 (1993); Teraoka, I.; Z. Zhou; Langley, K. H.; and Karasz, F. E. *Macromolecules* 26, 3223 (1993); Teraoka, I.; Z. Zhou; Langley, K. H.; and Karasz, F. E. *Macromolecules* 26, 6081 (1993); and "Interferometric Study of Concentration Equilibria of Polystyrene Solutions with a Porous Glass Bead" by I. Teraoka and A. Dube, an Abstract Submitted for the March 1994 American Physical Society (APS) Meeting held March 21–25 in Pittsburgh, Pa., the complete disclosures of which are hereby incorporated by reference.

The HOPC method uses as a separation mechanism the enhanced partitioning between the mobile phase and the stationary phase that takes place when the concentration of the mobile phase is semidilute, i.e., about equal to or higher than the overlap concentration, c*. Under this condition, high osmotic pressure is produced which drives polymer molecules into the pore channels where the osmotic pressure is lower. The forced migration takes place selectively in favor of low molecular weight components because of the confining geometry of the pores. Scaling concepts for overlapping polymer chains in polymer solutions and the meaning of the terms "dilute", "semi-dilute", and c* are discussed in F. W. Billmeyer's *Textbook of Polymer Science,* 3rd Ed. Wiley-Interscience, 1984 (Chapter 7), the complete disclosure of which is hereby incorporated by reference.

In the HOPC method, the semi-dilute or concentrated polymer solution is introduced onto the column of porous material at the column inlet via a high pressure pump, and lower molecular weight components are driven preferentially into pore channels. The osmotic pressure-driven separation process is repeated as the solution moves down the column, thereby enriching the front end of the transported polymer solution with the highest molecular weight components present in the original sample. Injection of a sufficiently concentrated solution keeps the front end of the mobile phase in the semidilute regime until solution reaches the outlet so that the enhanced partitioning is repeated at every plate on the column. Routine fractionation at the outlet can be then effected. Initial fractions collected at the column outlet thus consist of the highest molecular weight components.

A similar partitioning takes place for mobile phase that follows the initial fractions. When the mobile phase is transferred to the next plate in the column to reestablish concentration equilibrium, the stationary phase will release components of a molecular weight higher than those in the mobile phase which in turn will force the lower molecular weight components to migrate into the pore channels. Repeating this equilibration at every plate as the mobile phase moves toward the column outlet results in the mobile phase sweeping up the highest molecular weight components remaining in the column. Continuous injection of a large volume of the polymer sample in high concentrations maintains the high osmotic pressure condition.

It is critical that the concentration of the polymer component in the solvent is equal to, or preferably, greater than the overlap concentration, $c^*$. Preferably, the concentration is equal to or greater than twice, or more preferably, equal to or greater than thrice, the overlap concentration. There is no strict upper concentration limit. The only critical limitation is that the solution must still be a fluid. For purposes of the present invention, fluid is defined to mean the solution is not so viscous that it can not be transported by means of a pump at the temperature of HOPC operation. However, it is possible that when the concentration of the mobile phase is too high, at least some of the high molecular weight components will be driven into the stationary phase, resulting in a decrease in the separation resolution.

The minimum concentration, $c^*$, at which chain overlap occurs can be identified as the reciprocal of the intrinsic viscosity $[\eta]$ for the polymer sample. Intrinsic viscosity can be readily measured using a viscometer by methods known to those skilled in the art. For many common linear polymers, however, the measurement of the intrinsic viscosity is not necessary, because the intrinsic viscosity can, with the help of published data, be determined from molecular weight measurements using, for example, analytical GPC. The following equation, as known to those skilled in the art, can be used:

$$[\eta] = K'M^a$$

where $K'$ and superscript $a$ are published constants and $M$ is the molecular weight of the polymer. Concentrations of the polymer solution to be injected can typically range from about 2–50 wt. %. More preferably, the concentration can range from about 3–30 wt. %.

The osmotic pressures that can be generated by concentrated polymer solutions according to the present invention can be estimated as described by I. Noda et al. in *Macromolecules* 14, 668 (1981), the complete disclosure of which is incorporated herein by reference.

In principle, any polymer that can generate relatively high osmotic pressure when dissolved at concentrations of at least the overlap concentration can be fractionated by HOPC. The relatively high osmotic pressure is "high" with respect to the osmotic pressure produced by the solute polymer in an ideal solution of the same concentration. The polymers can be a synthetic organic, semi-organic, organometallic, or inorganic polymers. The polymers can also be natural polymers to the extent that they meet the above described critical feature of relatively high osmotic pressure upon exceeding the overlap concentration.

Preferably, the polymer should be molecularly dispersed in solution. However, it is recognized that at high concentrations, some polymer solutions might not be ideally molecularly dispersed in solution. For purposes of the present invention, the term "solution" should not be so rigidly construed. Some aggregation of polymer chains will not prevent successful execution of HOPC. A lack of molecular dispersion is not anathema to the present invention.

Representative synthetic organic polymers which can be fractionated by HOPC include, among others, polystyrene, poly(methyl methacrylate), polycarbonate, and poly(hexylisocyanate). However, the invention is not limited to these. Polycarbonate and especially poly(hexylisocyanate) have a relatively inflexible polymer backbone compared to polystyrene and poly(methyl methacrylate). Hence, the polymers that can be processed by the HOPC method are not limited to flexible chain polymers like polystyrene. Polar groups can be present in the polymer chain or side group.

In addition, polyolefins such as polyethylene and polypropylene that can be dissolved only at elevated temperatures can be fractionated if fluid paths in the HOPC system are maintained at high temperatures. Use of elevated temperature during chromatography should help reduce backpressure.

Other exemplary types of synthetic polymers include soluble polysiloxanes, polyphosphazenes, polysilanes, polyacrylates, polyamides, polyesters, polyurethanes, and the like, as known by those skilled in the art. The HOPC method is also suited to fractionating water-soluble polymers. In principle, polymers having polymerized units of saccharide, nucleic acid, amino acid, and the like can be fractionated by HOPC. Sulfuric acid-soluble polymers such as aromatic polyamides (e.g., Kevlar) can also be fractionated.

The number average molecular weight of the polymer to be fractionated can be greater than about 1,000 g/mol, and more preferably, is greater than about 10,000 g/mol, to ensure that sufficient osmotic pressure is generated. In general, the number average molecular weight can be up to about, for instance, $10^7$ g/mol although in principle, there is no strict upper limit to molecular weight. The molecular weight of the polymer can be as high as practically possible. Higher molecular weight, in principle at least, should generate higher osmotic pressures. Higher molecular weight also generates higher solution viscosities, and lower overlap concentrations.

Liquid crystalline polymers such as lyotropic polymers can be separated by HOPC, although liquid crystalline lyotropic phases, which occur with some rigid polymers when dissolved at higher concentrations, can be undesirable if liquid crystallinity results in a reduction of the osmotic pressure. Polymers that show solution structure or are in the form of a microscopic gel can be separated by HOPC to the extent high osmotic pressure is generated and steric exclusion can occur.

One particularly useful application of HOPC is the preparation of purified polycarbonates for use in the preparation of compact disks and the like. Compact disks prepared from polycarbonates and other transparent materials are described in the articles entitled "Polycarbonates" pgs. 648–718, *Encyclopedia of Polymer Science and Engineering* Vol. 11, 1988, John Wiley; "Compact Disk", McGraw-Hill *Encyclopedia of Science and Technology*, 7th Ed. pgs. 213–215, 1992; "A New Substrate for Portable Optical Disks", *Plastics Engineering*, April, 1995, pgs. 33–36 and "Information Storage Materials" pgs. 171–239, Ullmann's *Encyclopedia of Industrial Chemistry* Vol. A14, 1989, VCH, the complete disclosures of which are hereby incorporated by reference.

In a preferred embodiment for HOPC, the concentrated polymer solution is passed onto the column as follows. Polymer solution is passed, preferably by pumping, from a container of the solution onto the column until polymer can be detected at the column outlet. Then, the passing of the polymer solution through the column is stopped, and the passing of a pure solvent onto the column is started. Another method of introducing the polymer solution is to store the solution temporarily in a sample loop of large volume in an injection valve, followed by flushing the loop by the mobile phase. In this way, a given amount of polymer solution is pumped onto the column. The eluent is then collected and fractionated as pure solvent continues to be passed through the column until the eluent becomes pure solvent.

It is preferred that the injection volume of the polymer sample is about equal to the total mobile phase volume in the column. However, this preference is not a strict limitation, and the optimum volume of polymer sample can be determined by a person skilled in the art simply by adjusting the amount of solution passed onto the column before passing pure solvent through the column.

The solution is passed onto the chromatographic matrix imbibed with solvent until at least 50%, and preferably at least 80%, and more preferably at least 90%, and most preferably, at least essentially all of the matrix is in contact with the solution.

Solvent is used at three points in HOPC. A first solvent is used to dissolve the polymer sample for a mobile phase. A second solvent is used to pack the column and imbibe the porous material as a stationary phase. A third solvent is used to elute the polymer sample mobile phase from the porous medium after polymer is detected at the column outlet. These three solvents are preferably the same solvent, although it is possible that in some operations, the solvents might be different. Choice of solvent can be determined by the person skilled in the art. THF, cyclohexanone, and toluene are three preferred candidates for organic soluble polymers. Other examples include hexane, hydrocarbons, ketones, ethers, benzene, benzene derivatives, chlorinated solvents, and the like. The solvents are preferably thermodynamically good solvents for the polymer to be fractionated. Water can also be used for water-soluble polymers. Solvents should be purified to the extent needed.

The chromatographic matrix or column can be prepared by imbibing porous materials such as porous silica gel with a solvent by techniques known in the art. The surface of the porous material is preferably chemically treated to prevent adsorption of polymer onto the pore walls. For example, the chemical modification technique for porous silica is known to those skilled in the art, and one method using silane treatment is illustrated in the Examples.

Stainless steel or glass columns can be used. The porous materials are preferably packed in a cylindrical column, although other geometric shapes for housing the porous material are also possible.

The porous material can be a porous inorganic material like silica gel, although other porous inorganic materials besides silica gels can be used to the extent that high osmotic pressure can be developed, polymer adsorption can be avoided, and the porous material can withstand the conditions (e.g. high pressure) of the chromatographic method. It is known in the art that excessively high pressure can cause problems with some softer, organic porous materials.

The porous material can include porous glass beads or controlled pore glass therein. Crosslinked polystyrene and other organic matrices can be used if they can withstand the pressures needed to pass concentrated polymer solutions through the column.

In principle, porous materials useful for perfusion chromatography can also be used in the present invention as described in U.S. Pat. Nos. 5,019,270, 5,228,989, and 5,384,042, the complete disclosures of which are incorporated by reference.

At the outlet port of the column, a detector can be used to detect and measure the elution of the polymer. The detector can be a refractive index detector, an ultraviolet spectroscopic detector, or any other detector known to persons skilled in the art. If applicable, visual inspection of the eluent can also be used to determine the point in time at which the sample begins to elute. When the polymer has a refractive index different from that of the solvent, Schlieren texture or cloudiness will be evident to the naked eye.

After passing through the detector, if present, the eluent is fractionated preferably based on elution time and preferably until the last polymer comes off of the column. For example, a series of flasks can be used to collect the eluent, each flask being used to collect a given volume of solution. The contents of each flask can be analyzed by conventional analytical GPC methods, or other methods for determining molecular weight, to determine the molecular weight and molecular weight distribution of the polymer fraction. The polymer fraction can be isolated, for example, by removal of the solvent by evaporation, by precipitation, by freeze-drying, or by any other method known to those skilled in the art. In some applications, simple concentration or enrichment of the fraction may be desirable.

By the HOPC method, kits of narrow molecular weight distribution polymers can be prepared from these fractions. A kit can comprise a series of samples of the same polymer in which each sample has a different molecular weight and preferably has a narrow molecular weight distribution. A kit is useful in, for example, standardizing analytical instruments. The use of HOPC, which produces large amounts of purified material coming off the column of continuously decreasing molecular weight, allows kits to be prepared for a wide variety of polymers, including polymers that cannot be prepared by anionic polymerization.

The HOPC method can be applied repeatedly to the polymer fractions obtained in previous runs. By combining fractions from several preceding batches, which fractions have a similar molecular weight distribution, a concentrated solution above the overlap concentration can be again prepared and injected onto the column. The molecular weight distribution will be narrowed further, with no inherent ultimate limitation due to conventional GPC band broadening. As a rough rule, the PDI of an isolated sample from one HOPC run can be estimated to be about the square root of the PDI of the original sample loaded onto the column.

Therefore, HOPC can be used to fractionate polymer samples further that already have a relatively narrow molecular weight distribution such as, for example, common commercially available polystyrene, poly(methyl methacrylate), or polycarbonate standards prepared by conventional anionic polymerization, fractional precipitation, or the like.

HOPC can be, in principle, practiced more effectively with use of columns placed in series (cascade effect). The eluent is simply passed onto another chromatographic matrix. Alternatively, recycling of the eluent onto the same column can be effected. The HOPC method can be, in principle, combined with other purification methods in a larger process scheme.

Typical HOPC chromatographic conditions like column size, flow rates, bead size etc. for bench scale experiments are provided in the Examples.

A relatively longer column is preferred in the HOPC method to achieve a larger number of theoretical plates with improved separation, but such length also produces a higher backpressure. When a longer column is used, a higher concentration of the injection sample is preferred to keep the mobile phase in the semidilute regime until the polymer elutes from the column outlet. The column diameter can be increased to increase the processing capacity and to reduce the backpressure.

A higher flow rate for the passing of the solution through the column will create the situation, at least in principle, wherein the mobile phase is transferred to the next plate before it reaches equilibrium with the stationary phase. However, since the low molecular weight components diffuse faster into the stationary phase than the higher molecular weight components do, a non-equilibrium condition can, at least in principle, actually improve the separation. A higher flow rate also results in a shorter processing time, if the HOPC system can withstand the corresponding increased backpressure. The flow rate can be adjusted to obtain the best overall performance, paying attention both to the processing time and to the resolution.

In addition, when solvent is passed through the porous material, a higher flow rate is preferred to avoid creation of a solvent channel when the solvent replaces the solution previously passed onto the column. A large difference in viscosity between the concentrated solution that is present in the column and the solvent that is freshly pumped is considered at least to some extent to cause this problem. In contrast, when the concentrated solution of polymer is injected into the column, fewer problems with channel creation are observed.

As is well-known in conventional GPC practice, it is critical that the pore size, or pore openings, of the porous materials packed into a chromatographic matrix should be of a dimension approximately equal to the average molecular size of the polymer chain, so as to exert a confinement effect that strongly depends on the chain size. The chain size or molecular size as represented by the hydrodynamic volume, the radius of gyration, and the like, can be determined by a person skilled in the art. At least in principle, the pore size must not be too small or too big. A small pore size imposes a longer equilibration time at each plate, as diffusion of polymer molecules into the porous medium slows down. A large pore size will not allow for selective size exclusion. Pore openings have an average diameter between about 4–100 nm, and more preferably, between about 5–30 nm.

Separation at each plate will, at least in principle, improve if the porous materials have a cylindrical pore of a single, constant diameter. Such materials include nano-channel array glasses manufactured by repeating the elongation and bundling of optical fibers followed by acid leaching of the core glasses.

The nano-channel array glasses are described by R. J. Tonucci, B. L. Justus, A. J. Campillo, and C. E. Ford in *Science* 258, 783 (1992), as well as in U.S. Pat. No. 5,234,594, the complete disclosures of which are hereby incorporated by reference. Also included are mesoporous inorganic solids produced in calcination of silicate gels in the presence of surfactants that form micelles in hexagonal packing. The latter is described in the article by C. T. Kresge, M. E. Leonowicz, W. J. Roth, J. C. Varful; and J. S. Beck in *Nature* 359, 710 (1992) and in U.S. Pat. No. 5,057,296, the complete disclosures of which are hereby incorporated by reference.

Porous materials can be purchased as beads, and the bead size of the porous materials for HOPC can be adjusted. At least in principle, the smaller bead will accelerate equilibration of the concentrated polymer solution with the pore at every plate, which will allow increased flow rate and improve the overall efficiency of the HOPC. The smaller bead size, however, will increase the backpressure.

There is no strict limit as to bead size. However, it is preferred that bead diameter be less than one millimeter to maximize resolution.

The ratio of the external volume (interstitial volume) in the column to the internal volume (pore volume) can be increased by mixing solid, nonporous particles with porous silica gels or by using porous materials with a smaller specific pore volume. Partitioning at each plate can, at least in principle, depend on this ratio.

The flow rate as a function of time for the injection of the polymer solution and for the injection of the solvent can be programmed and optimized by a person of skill in the art.

The packing of porous materials in the column can also be adjusted by a person of skill in the art. For example, the upstream and downstream portions of the chromatographic matrix can have a different pore size or a different ratio of the exterior to interior volume.

For aqueous HOPC application, the addition of salts to the mobile phase and the solvent can affect separation performance. Such modifications to the mobile phase can be executed by a person of skill in the art.

For a large processing scale, a pump that can deliver a viscous solution at a relatively high flow rate and against a large backpressure is preferred. For example, a syringe pump as used in supercritical fluid chromatography can be used. Suitable pumps are disclosed in U.S. Pat. Nos. 3,855,129 and 4,422,942, the complete disclosures of which are hereby incorporated by reference.

The present invention for HOPC can also be applied to the separation of polymer blends. A mixture of two polymers can be difficult to separate macroscopically. In principle, the separation can be accomplished by the application of HOPC to a polymer mixture dissolved in a common solvent. For example, the stationary phase can be nonporous silica beads or porous materials of large pore size having surfaces modified to attract one of the polymer components selectively. At high concentrations, one of the polymers will be pushed into the stationary phase by the repulsion of the other polymer. The difference in the affinity of the surface of the stationary phase to the constituent polymer will determine which of the two polymers is attracted to the stationary phase. The injected solution can be in a single-phase regime or in a two-phase regime (phase separated). Even in a single phase regime, the two polymers show large spatial fluctuations in the composition. With the help of the difference in the interactions with the stationary phase, segregation will occur between the mobile phase and regions close to the stationary phase. Polymers partitioned to the mobile phase will elute faster.

By the same principle, copolymers having different composition can be separated. Also possible would be separation of polymers having different degrees of branching, polymers with different stereoregularity, block branch or graft copolymers, and polymers of other microscopic architecture, as known to those skilled in the art.

The HOPC process described in the Examples for bench scale operations can be completed in a relatively minimal amount of time, typically 1–3 hours, depending on experimental conditions. Hence, multiple separations at this level can be effected in one work day.

A person skilled in the art can use the HOPC method to isolate or study any component passed through the porous material, whether the component is of low or high molecular weight, and whether the component causes or does not cause the high osmotic pressure.

In addition to HOPC, enhanced partitioning fractionation (EPF) is another embodiment of the present invention. EPF utilizes the above-described principle of high osmotic pressure enhanced fractionation, but EPF is not a chromatographic process.

The publication by A. Dube and I. Teraoka in *Macromolecules* 28, 2592 (1995) describes an exemplary EPF process, the complete disclosure of which is hereby incorporated by reference. The EPF process is also illustrated in the article by A. Dube and I. Teraoka entitled "Weak-To-Strong Penetration and Its Application to Fractionation of Polymers" to be published in Waters *International GPC Symposium '94* (Waters Corp.), pg. 547, 1994, the complete disclosure of which is hereby incorporated by reference.

The full EPF process consists of two distinct stages. The first stage is critical. The second stage is optional, but preferred.

In the first stage, a semidilute solution is provided having a polydisperse polymer component therein. The polymer solution is contacted with solvent-filled porous material that has pore openings that allows for size-based (hydrodynamic volume-based) partitioning of the polymer component. The concentration of the polymer component is about equal to or greater than the overlap concentration of the polymer component. The partitioning is allowed to approach or reach equilibrium. Then, the polymer component is separated from the porous material. The separation of the polymer component results in a solution enriched in higher molecular weight portions of the polymer component, which can be isolated from or concentrated in the solution.

In the optional second stage of EPF, the separation of the polymer component from the porous material is followed by contacting the porous material with a solvent which extracts lower molecular weight portions of the polymer component from the porous material to yield another solution enriched in lower molecular weight portions of the polymer component. This second solution can be separated from the porous material, and the lower molecular weight component can be isolated from or concentrated in the solution.

The descriptions given thus far for the HOPC method concerning, for example, concentration of sample, selection of polymer, pore size, bead diameter, selection of porous material, pretreatment of porous material etc. are, at least to some extent applicable to the EPF process, although EPF is not a chromatographic process. The EPF process can be executed in several embodiments.

For example, the EPF process can be executed with porous beads such as relatively large beads of about two mm in diameter. However, more preferably, the EPF process can also be effected with use of controlled pore glass or silica gel consisting of porous beads or particles of much smaller diameter. Controlled pore glass is available from, for example, CPG Inc. Silica gel (Davisil®) is manufactured by Davison of W. R. Grace.

Preferably, the bead diameter for EPF is less than about 0.5 mm. The unexpected advantages that accrue with use of glass having smaller bead size, as illustrated in the Examples, include processing time reduction and better separation resolution.

A further embodiment of the EPF process, as illustrated in the Examples, involves using a pump to circulate the solutions through the porous materials. However, in this embodiment of EPF, fractionation is not effected as for HOPC. The use of a pump in EPF results in the ability to use higher concentrations of polymer solution.

In principle, EPF can be effected in an additional embodiment by providing a polydisperse polymer melt or oil. The melt can be contacted with the porous material having pore openings that allow for selective migration of high and low molecular weight components in the melt. Outside the porous material, the melt or oil is thereby enriched in higher molecular weight components, which can be separated from the porous material. Optionally, the porous material can then be washed with a solvent to extract out the lower molecular weight components. The extracted lower molecular weight components can then be separated from the porous material.

When EPF is effected with a melt or oil, the bead diameter is preferably less than about 0.5 mm. Exemplary melts or oils include lower molecular weight polysiloxane mixtures. In this embodiment, dry porous material not imbibed with solvent is used. The solvent used to extract the lower molecular weight components can be any solvent that dissolves the polymer or any other low molecular weight liquid that mixes with the polymer.

The following examples are meant to illustrate the present invention, but the invention is not limited thereto.

EXAMPLES

Materials and Methods

All molecular weights reported herein were either provided by the supplier or were measured by GPC analysis by standard GPC methods using polystyrene reference standards. The GPC analysis of the fractions was carried out using a conventional Waters GPC system with a model 510 HPLC pump, Styragel columns (HR 4E, HR 5E, and HMW 6E), and a model 410 differential refractometer. The mobile phase was THF, and the flow rate was 1.0 mL/min.

Treatment of the silica to Minimize Polymer Adsorption

All silica gels for both EPF and HOPC were pretreated with trimethylchlorosilane to minimize adsorption of polymer to the silica surface. The pretreatment procedure is given below:

1) Silica beads were soaked in concentrated nitric acid at 50°–90° C. overnight to remove organic impurities. The beads were rinsed thoroughly with deionized water until the water rinsings were neutral.

2) Silica beads were soaked overnight in concentrated hydrochloric acid at room temperature to remove metal ions and to activate the silica surface for silanation. The beads were again rinsed with deionized water until neutral.

3) Silica beads were dried in a convection oven at 50° C. for 6 hours, and then at 90° C. for 24 hours. The beads were then dried at 220° C. in vacuum for four hours and allowed to cool to room temperature.

4) Silica beads were transferred into a three-neck flask equipped with a thermometer, nitrogen inlet, and ventilation stopcock. A solution of trimethylchlorosilane in toluene (2M) was added to the flask together with a nitrogen purge. The flask was heated to 50°–60° C. The stopcock was closed. The flask was kept at this temperature for about 72 hours.

The minimum requirement of the silanation agent was calculated from the surface density of silanol, one functionality per 10 Å$^2$. The actual amount added was about 15 times this minimum requirement.

5) The reaction was quenched by adding filtered methanol. The silica was washed with methanol until pH neutral. Drying was executed at 50° C. in a convection oven overnight. Drying was further carried out at 210° C. in vacuum for one hour.

Packing the Column for HOPC

1) An end-capped, glass or stainless steel (SS) column was fixed to a vertical support. Surface-treated, freshly dried silica gels were added through the top, open end of the column. The column was connected to a high pressure liquid pump (Scientific Systems Inc., SSI, AcuFlow Series II) with use of Teflon or SS tubing.

2) A polar solvent such as cyclohexanone or tetrahydrofuran was circulated through the column at a high flow rate. Cyclohexanone is nearly isorefractive with silica. Hence, when the air was removed, the packed glass column was nearly transparent.

3) When a space was created over the packed bed of silica gels in the column, the top fitting was removed and additional dried silica gel was added. The fitting to the top was connected, and the solvent was circulated.

4) Step 3 was repeated until no space was left in the column.

EXAMPLE 1

HOPC with Polystyrene Sample

Reference is made to FIG. 1. A SS chromatographic column (3.9 mm internal diameter, ID, 300 mm length) was packed with silica gel (Davisil®) having 37 μm bead size and 15 nm pore size. The silica gel was washed with tetrahydrofuran (THF).

A solution (20.7 wt %) of polystyrene dissolved in THF was prepared. The polystyrene (Aldrich) had a weight-average molecular weight, Mw, of $2.5 \times 10^5$ and a number-average molecular weight, Mn, of $9.6 \times 10^4$ (polydispersity index Mw/Mn=2.6).

The polystyrene solution (1.6 g) was introduced onto the silica gel column and forced through the column with a high pressure pump at a flow rate of 0.1 mL/min. When polystyrene was detected at the column outlet, pure THF was pumped through the column at a flow rate of 0.1 mL/min, and material eluting from the column was fractionated. A total of 26 fractions were collected.

Figure 2:
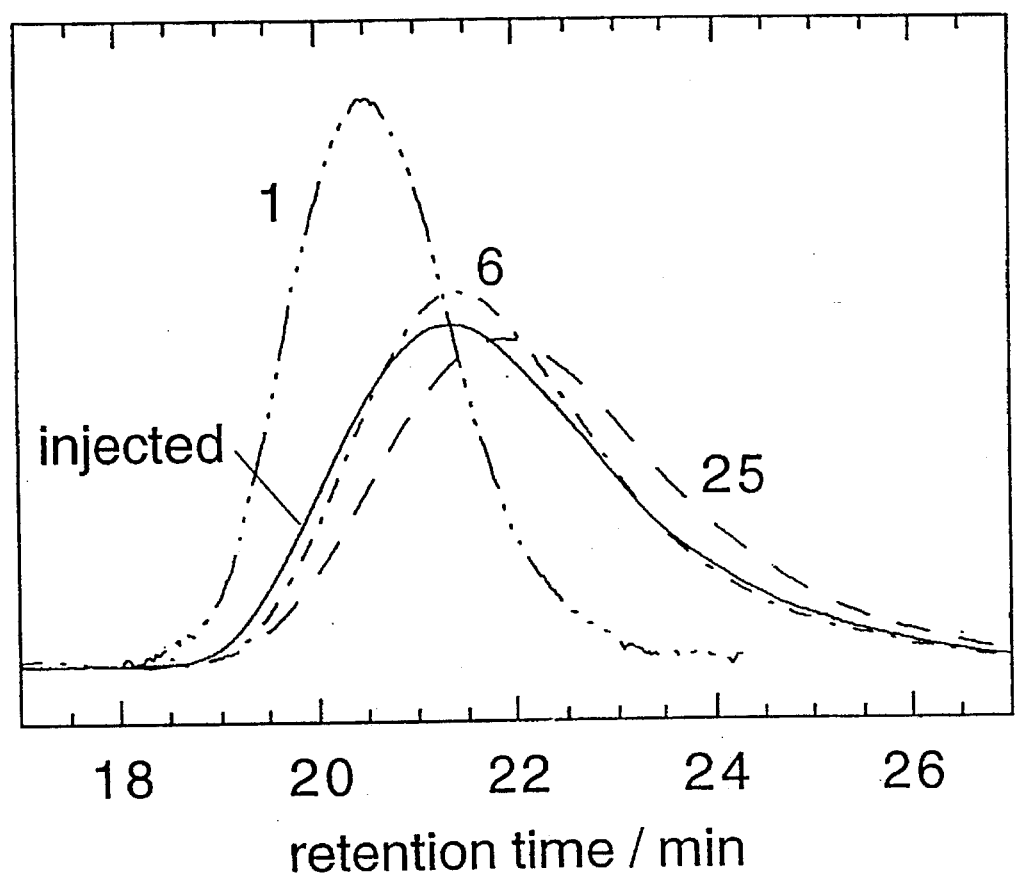
FIGS. 2–5 demonstrate the performance of HOPC.

In FIG. 2, the GPC analysis of the molecular weight distribution of the original polystyrene sample, as first injected, is shown in comparison with collected fractions 1, 6, and 25. The earlier fractions are enriched with high molecular weight polystyrene, and later fractions are enriched with low molecular weight polystyrene.

EXAMPLE 2

HOPC with Purified Polystyrene Sample

A glass chromatographic column (10 mm ID, 500 mm length) was packed with silica gel (Davisil®) having 100 μm bead size and 15 nm pore size. The silica gel was washed with cyclohexanone.

A solution of polystyrene in cyclohexanone (23.7 wt %) was made by combining multiple fractions obtained in preceding batches of HOPC applied to the original polystyrene sample received from Aldrich (Example 1). The combined fractions had similar peak retention times. The solution was injected at 0.01 mL/min, and as soon as the polymer was detected the pumping was switched to cyclohexanone at 0.06 mL/min. A total of 12 fractions were collected.

Figure 3:
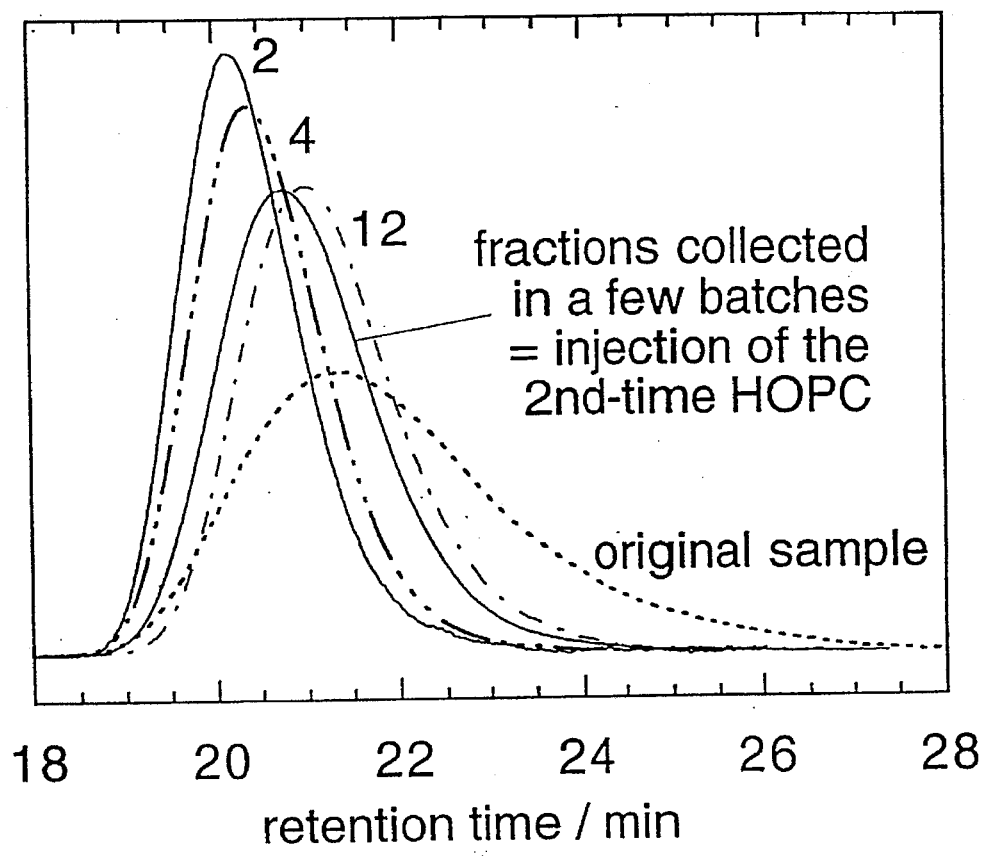

In FIG. 3, the GPC analysis of the molecular weight distributions of the original polystyrene sample and the polystyrene injected in the current processing is shown in comparison with fractions 2 and 4, which are enriched in high molecular weight polystyrene, and fraction 12, which is enriched in low molecular weight polystyrene. The molecular weight distribution narrowed further by repeated application, especially for initial fractions.

EXAMPLE 3

HOPC with Polystyrene Standard

A SS chromatographic column (3.9 mm ID, 300 mm length) was packed with silica gel (Davisil®) having 37 μm bead size and 15 nm pore size. The silica gel was washed with THF. A solution of a polystyrene standard (Mw=$9.1 \times 10^5$, Mn=$6.1 \times 10^5$; (Pressure Chemical) dissolved in THF was prepared. The concentration was 8.0 wt. %.

The polystyrene solution (1.7 g) was introduced onto the silica gel column as described previously and forced through the column with a pump at a flow rate of 0.1 mL/min. When the polystyrene was detected at the column outlet, pure THF was pumped through the column at a flow rate of 0.1 mL/min, and material eluting from the column was collected (total 20 fractions).

Figure 4:
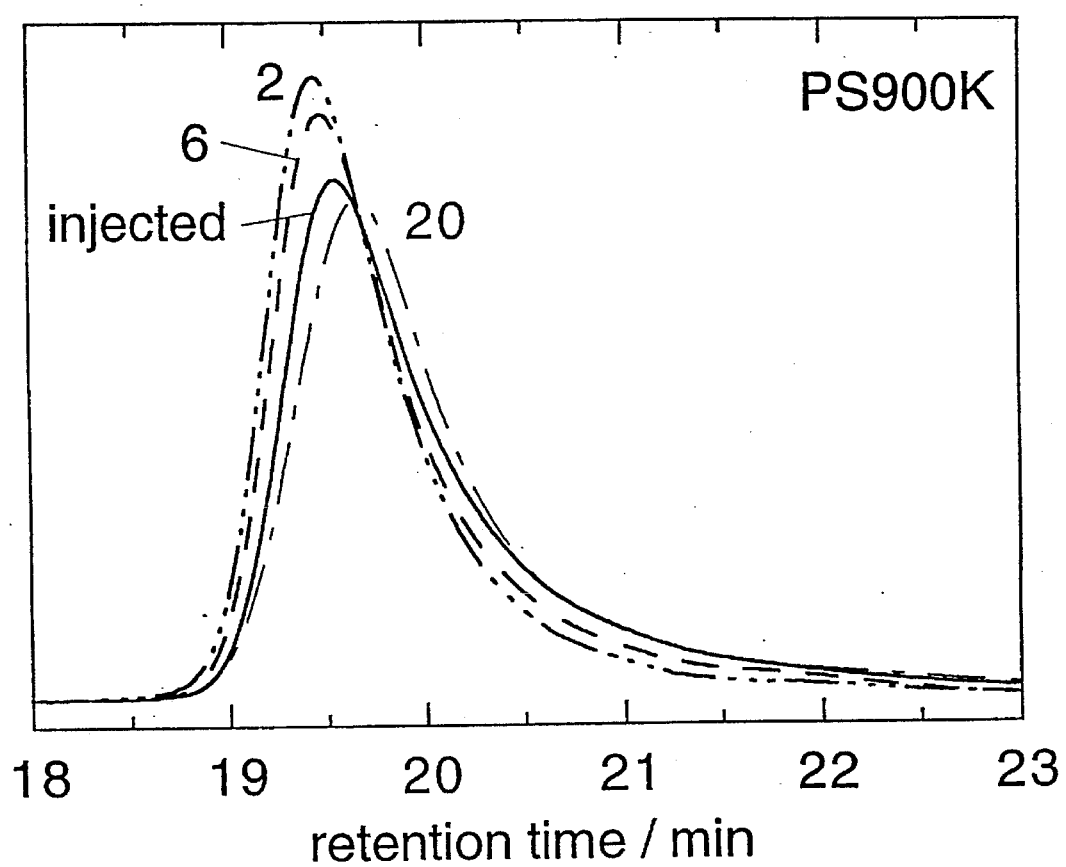

In FIG. 4, the GPC analysis of the molecular weight distribution is shown for fractions 2, 6, and 20, and for the original polystyrene sample, as first injected. Note that the GPC analysis system employed does not have the resolution to analyze the molecular weight distribution of fractions that have already a narrow distribution. Nevertheless, FIG. 4 shows that the fractions obtained in HOPC have retention times shorter and longer than the retention time for the injected sample. The peak retention time shifts to a longer time as the count of the fraction increases.

EXAMPLE 4

HOPC with Polystyrene Standard

A SS chromatographic column (3.9 mm ID, 500 mm length) was packed with silica gel (Davisil®) having 37 μm bead size and 15 nm pore size. The silica gel was washed with THF. A solution of a polystyrene standard (Mw=$1.9 \times 10^6$; Mn of $1.2 \times 10^6$; (Pressure Chemical) dissolved in THF (8.0 wt %) was prepared.

The polystyrene solution (1.8 g) was introduced onto the silica gel column and forced through the column with a pump at a flow rate of 0.1 mL/min. When the polystyrene was detected at the column outlet, pure THF was pumped through the column at a flow rate of 0.1 mL/min, and material eluting from the column was fractionated. A total of 24 fractions were collected.

Figure 5:
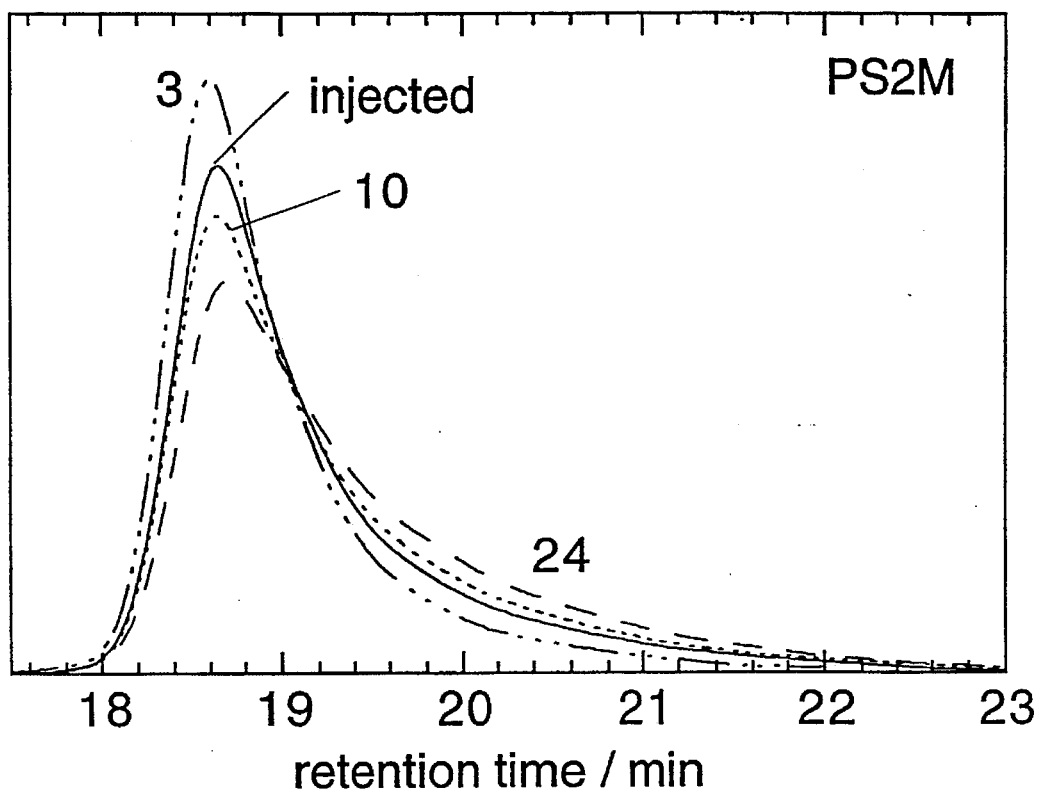

In FIG. 5, the GPC analysis of the molecular weight distribution of the original polystyrene sample, as first injected, is shown in comparison with fraction 3, which is enriched in high molecular weight polystyrene, and fractions 10 and 24, which are enriched in low molecular weight polystyrene.

EXAMPLE 5

HOPC with Poly(methyl methacrylate) Sample

A SS chromatographic column (3.9 mm ID×300 mm length) packed with silica gel (Davisil®) having 37 μm bead size and 15 nm pore size. The silica gel had been washed with THF.

Figure 6:
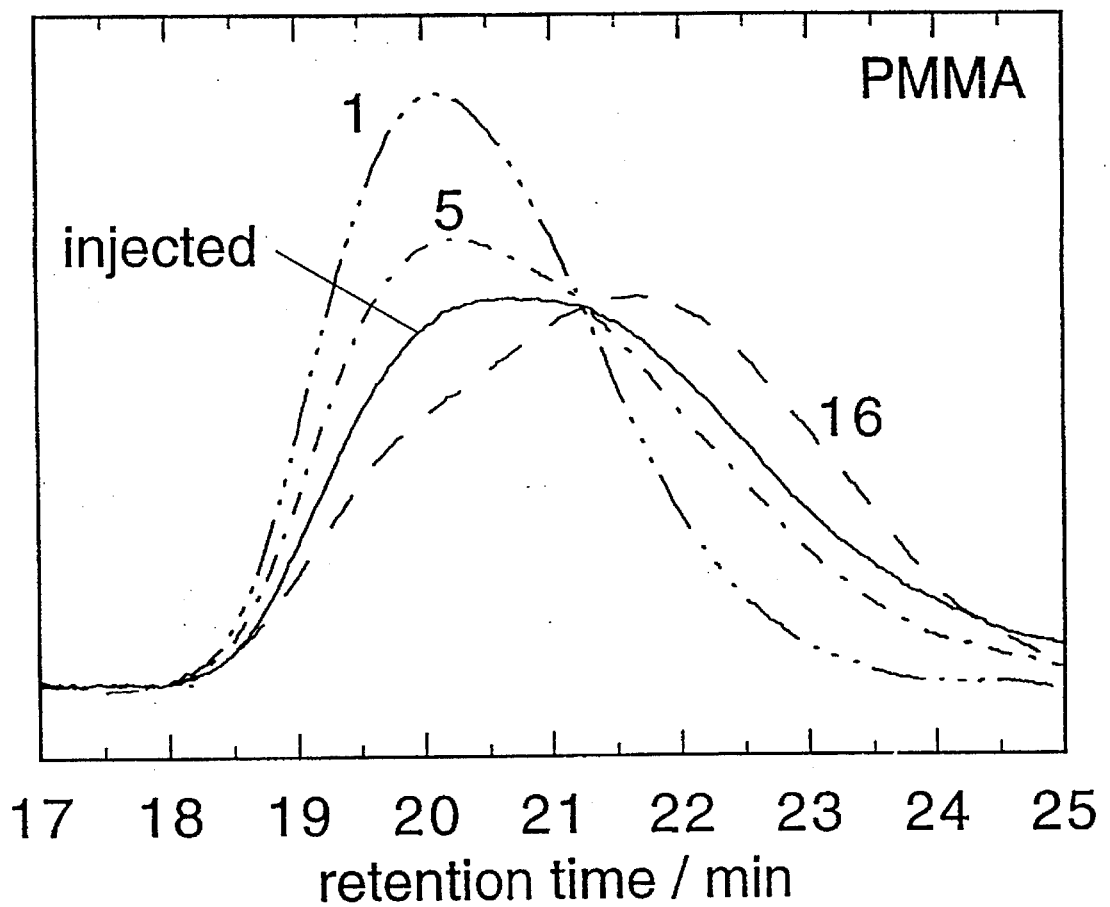

HOPC was applied to a 9.9 wt % solution of poly(methyl methacrylate) (PMMA) in THF. The PMMA had Mw =$5.1 \times 10^5$ and Mn=$1.5 \times 10^5$ (with reference to polystyrene). The PMMA solution (2.05 g) was introduced into the column at an injection rate of 0.1 mL/min until the polymer was detected at the column outlet. The injection was then switched to solvent at a flow rate of 0.1 mL/min. FIG. 6 shows the GPC chromatograms for fractions 1, 5, and 16 (total 16 fractions) and for the original PMMA injected.

Clearly, the HOPC method can be applied to polymers other than polystyrene.

EXAMPLE 6

HOPC with Polycarbonate Sample

A SS chromatographic column (3.9 mm ID, 330 mm length) packed with silica gel (Davisil®) having 37 μm bead size and 15 nm pore size. The silica gel had been washed with cyclohexanone.

Figure 7:
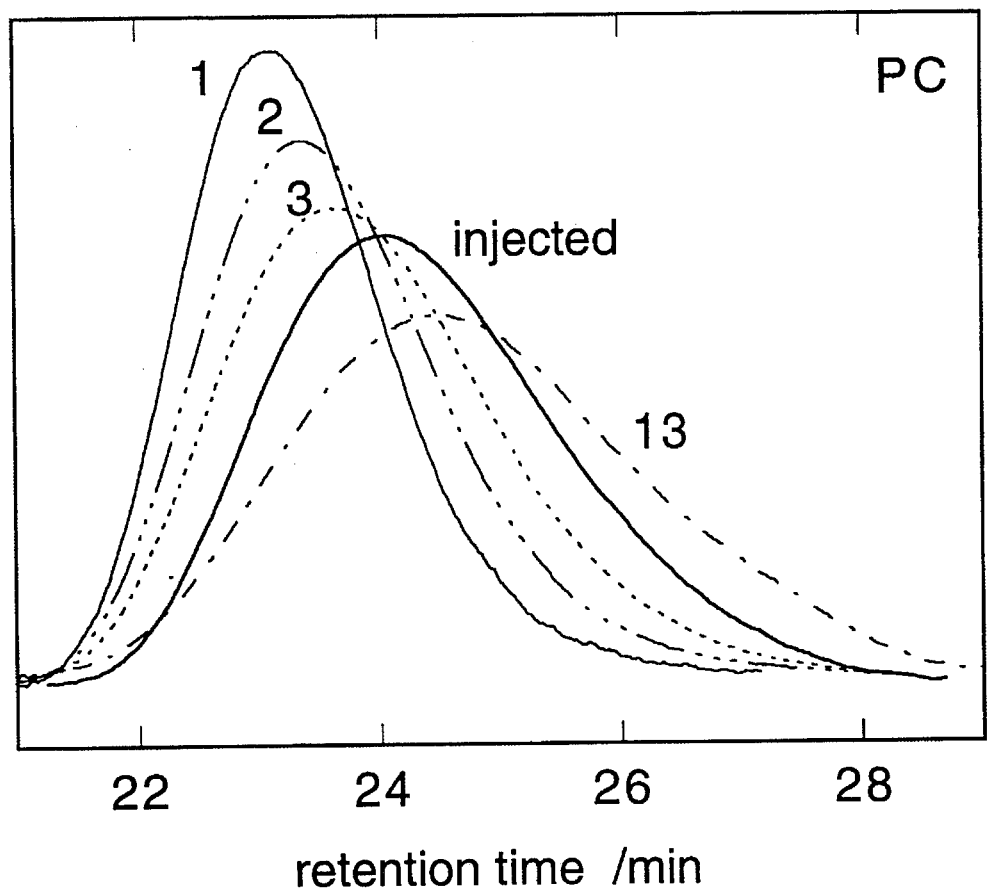

HOPC was applied to a 10.0 wt % solution of polycarbonate (PC; General Electric) in cyclohexanone. The PC had Mw=$4.7 \times 10^4$ and Mn=$2.5 \times 10^4$ (with reference to polystyrene). The PC solution (2.2 g) was introduced into the column at the injection rate of 0.1 mL/min. Then, the injection was switched to the solvent at 0.1 mL/min. FIG. 7 shows the GPC chromatograms for fractions 1, 2, 3, and 13 (taken from a total of 18 fractions) and for the original PC injected.

The process can be repeated until polycarbonate having PDI less than about 1.5 is prepared. Polycarbonate having PDI less than about 1.2 can also be prepared by repeated processing. Polycarbonate having PDI less than about 1.1 can be prepared by further processing. The polycarbonate is processed into the form of a disk and converted to a compact disk.

EXAMPLE 7

HOPC with poly(hexylisocyanate)

A SS chromatographic column (3.9 mm ID×300 mm length) packed with silica gel (Davisil®) having 37 μm bead size and 15 nm pore size. The silica gel had been washed with cyclohexanone.

HOPC was applied to a 7.9 wt % solution (not concentrated enough to be nematic) of poly(hexylisocyanate) (PHIC; Polysciences) in THF. The PHIC had $Mw=3.3\times10^5$ and $Mn=6.7\times10^4$ (with reference to polystyrene). The PHIC solution (1.6 g) was introduced into the column at the injection rate of 0.05 mL/min until the polymer was detected at the outlet. Then, the injection was switched to the solvent at 0.1 mL/min.

Figure 8:
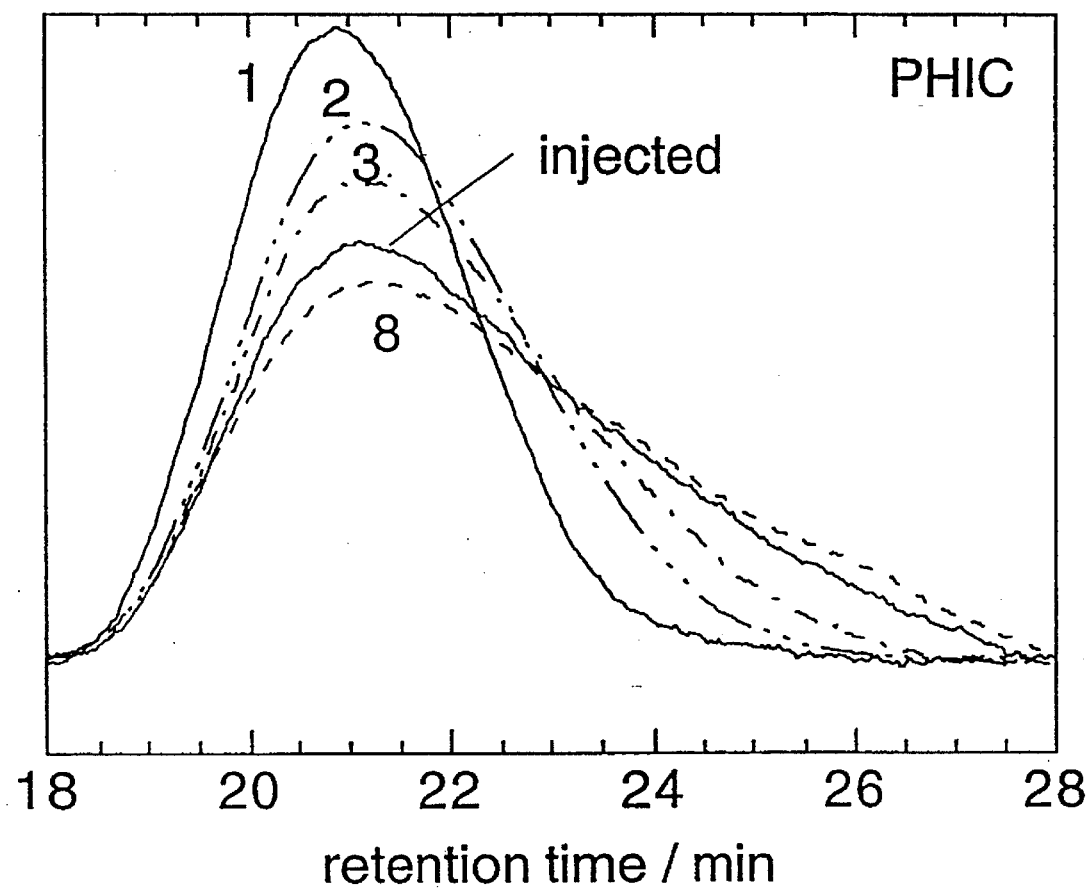

FIG. 8 shows the GPC chromatograms for fractions 1, 2, 3, and 8 (taken from a total of 31 fractions) and for the original PHIC injected.

EXAMPLE 8

Concentration Dependence, HOPC

A SS column of ID 3.9 mm and length 300 mm was used to see the effect of the concentration of the polymer solution on the separation performance of HOPC. The columns were packed with silica gel (Davisil®) with bead size 37 μm and pore size 15 nm. The packing density of silica gels is slightly higher in Examples 8 and 9 than in Examples 10 through 14. Four different concentrations (10.0, 15.0, 20.7, and 30.0 wt %) of polystyrene (Mw: $2.5\times10^5$, Mn: $9.6\times10^4$) dissolved in THF were prepared. Each solution was injected at 0.1 mL/min and, as soon as the polymer was detected, the injection was switched to the solvent THF at 0.1 mL/min.

A plot of the half width $t_w$ (width at half of peak height) of the GPC chromatogram as a function of the peak retention time $t_p$ for fractions collected is considered to represent the separation performance of each batch. Two features are important. One is the span of $t_p$ for all the fractions obtained. A wider span is considered better. The other is the absolute value of $t_w$ for a given $t_p$. A fractionation with its $t_w$-$t_p$ curve located lower implies a better separation (showing narrower half widths for the same peak height).

Figure 9:
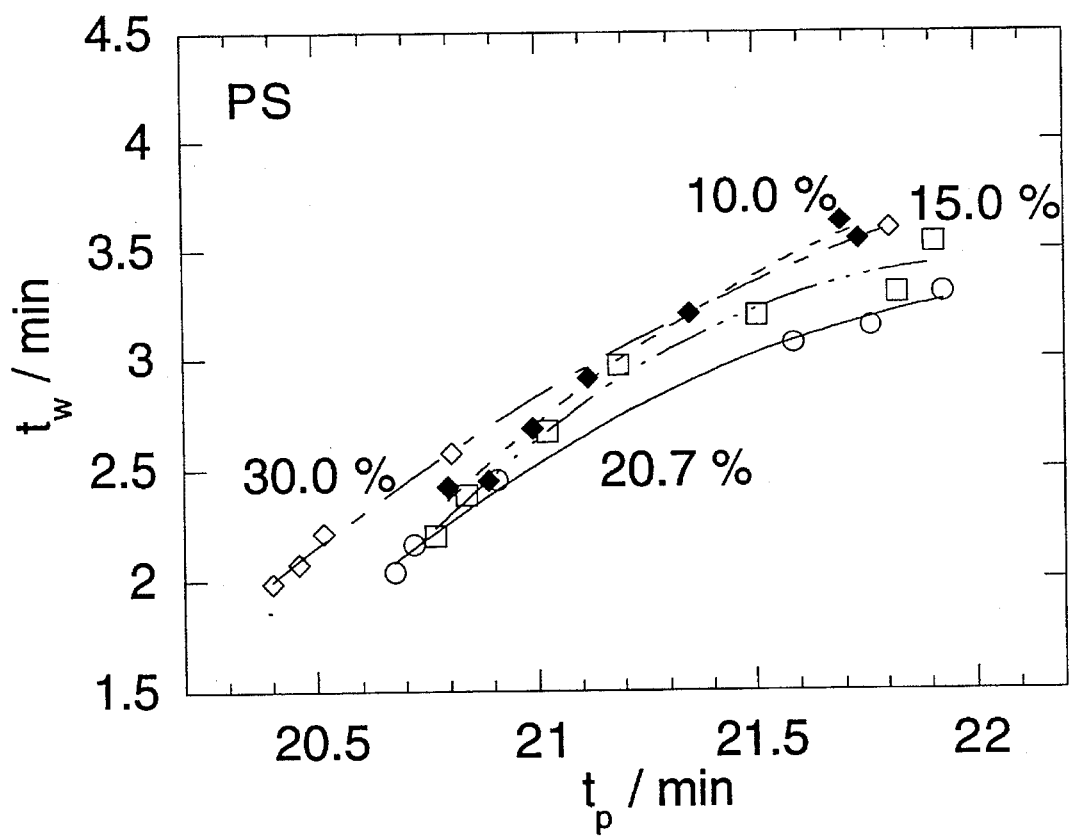

FIG. 9 shows the $t_w$-$t_p$ plot for the four concentrations. As the concentration decreases, the space of $t_p$ becomes smaller, and $t_w$ for later fractions increases. In the initial fractions ($t_p<21$ min), the 30.0 wt % solution shows the smallest $t_p$, but $t_w$ is larger than other concentrated solutions compared at the same tp, indicating relatively less effective resolution. It is evident that there is an optimal concentration which can be determined by those skilled in the art for a given system.

EXAMPLE 9

Injection volume Dependence, HOPC

A SS column of ID 3.9 mm and length 300 mm was used to study the effect of the volume of solution injection on the separation performance. The columns were packed with silica gel (Davisil®) with bead size 37 μm and the pore size 15 nm. A solution (20.7 wt. %) of polystyrene (Mw: $2.5\times10^5$, Mn: $9.6\times10^4$) in THF was injected at 0.1 mL/min. Various amounts, 0.50, 1.23, 2.05, and 3.06 g of the polymer solution were injected at 0.1 mL/min, before the injection was switched to the solvent THF at 0.1 mL/min. Note that in the batch injection of 2.05 g, the injection was switched from solution to solvent as the first polymer was detected at the column outlet.

Figure 10:
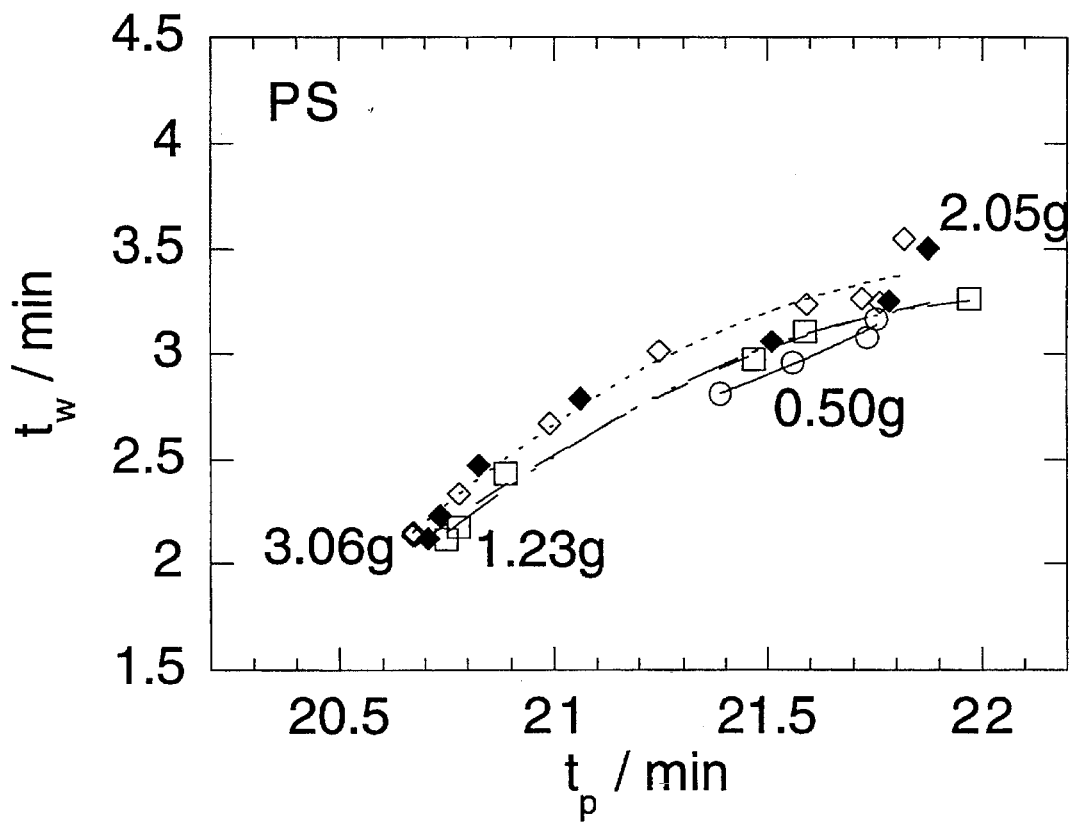

FIG. 10 shows the $t_w$-$t_p$ plot for the four injection volumes. As the injection volume decreases, and thus approaches the situation in the conventional GPC, the span in $t_p$ shrinks. An injection volume larger than the preferred amount degrades the performance for later fractions only slightly.

EXAMPLE 10

Column Length Dependence, HOPC

Three SS columns of the same ID (3.9 mm) but with different lengths (200, 300, and 500 mm) were used to study the dependence of the HOPC performance on the column length. The columns were packed with silica gel (Davisil®) with bead size 37 μm and the pore size 15 nm. A 20.7 wt. % solution of polystyrene (Mw: $2.5\times10^5$, Mn: $9.6\times10^4$) dissolved in THF was prepared. The solution was injected at 0.1 mL/min and, as soon as the polymer was detected, the injection was switched to the solvent THF at 0.1 mL/min.

Figure 11:
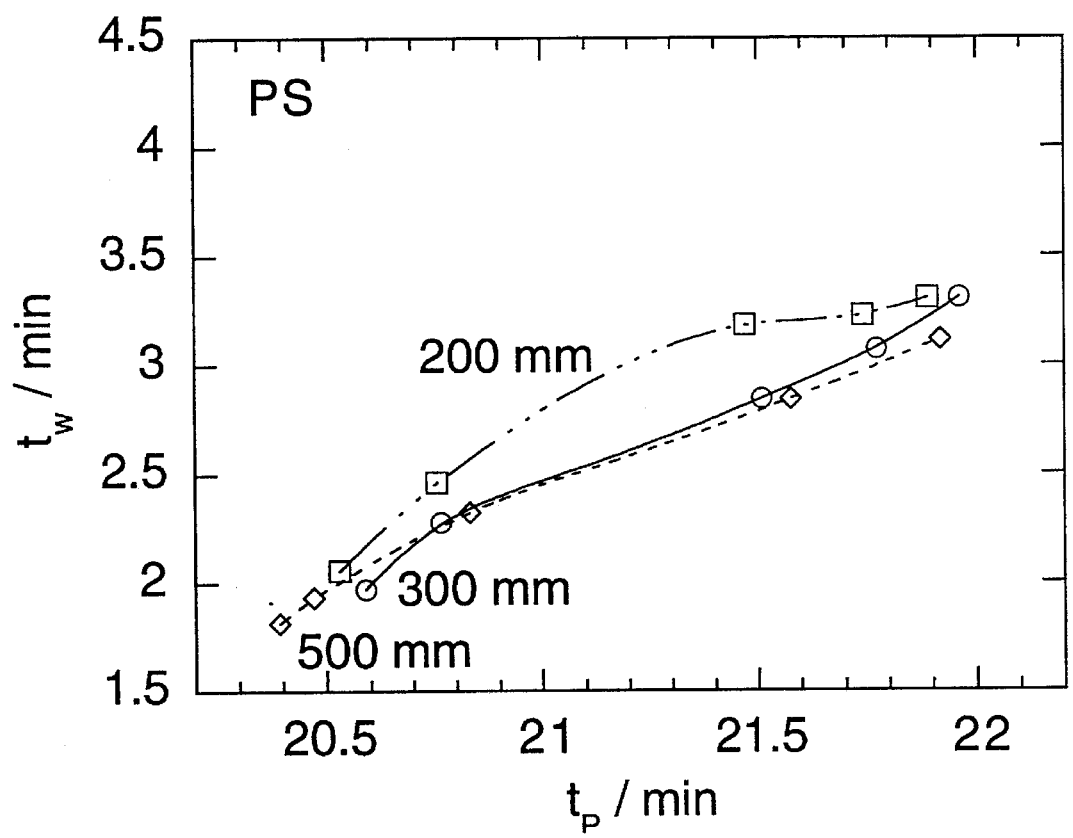

FIG. 11 shows the $t_w$-$t_p$ plot for the three lengths of the column. The performance of the 500 mm column is the best as expected with its span in $t_p$ the largest and the $t_w$-$t_p$ curve lying lowest. The shortest column show the worst performance in both the span in $t_p$ and the absolute value of $t_w$.

EXAMPLE 11

Solution Injection Rate Dependence, HOPC

A SS column of ID 3.9 mm and length 300 mm was used to study the effect of the solution injection rate on the separation performance. The columns were packed with silica gel (Davisil®) with bead size 37 μm and the pore size 15 nm. A solution (20.7 wt %) of polystyrene (Mw: $2.5\times10^5$, Mn: $9.6\times10^4$) in THF was injected at 0.05, 0.1, 0.2, and, 0.3 mL/min and, as soon as the polymer was detected, the injection was switched to the solvent THF at 0.1 mL/min (0.2 mL/min for the last batch of 0.3 mL/min solution rate).

Figure 12:
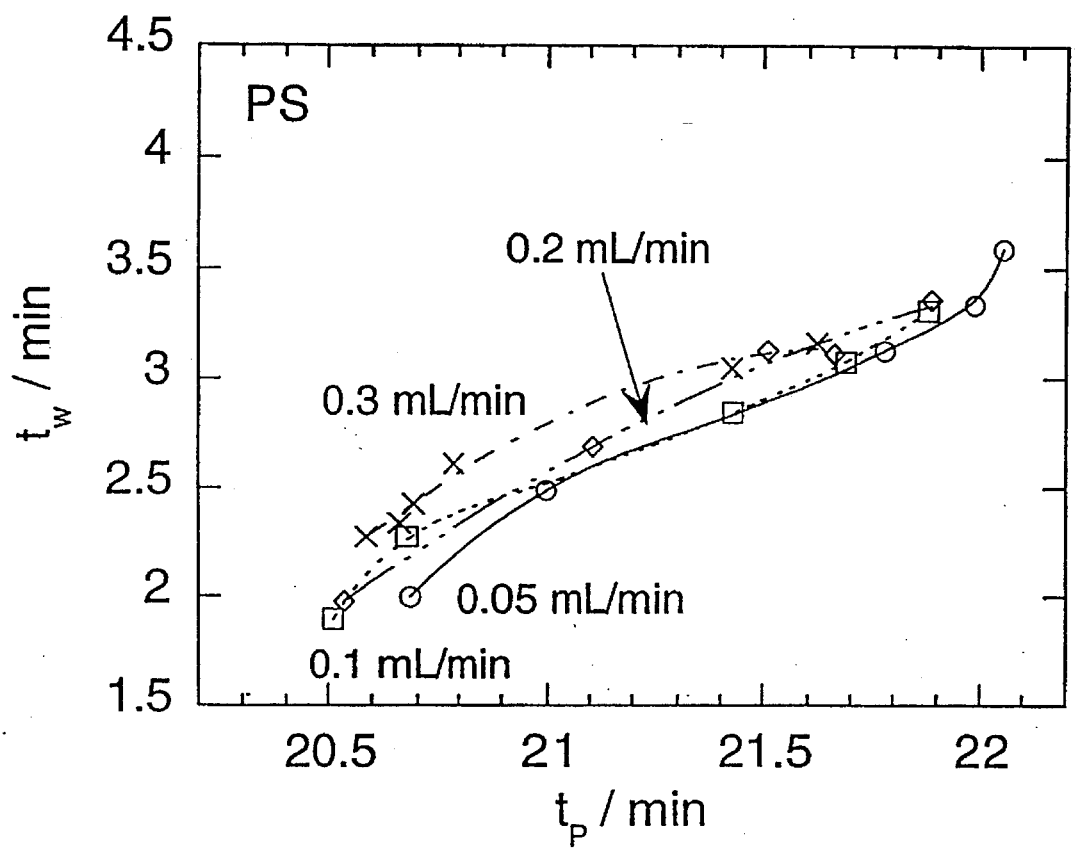

FIG. 12 shows the $t_w$-$t_p$ plot for the four solution injection rates. Faster injection rate decreased the span in $t_p$ and the purity. There was not significant difference between the two lowest injection rates.

EXAMPLE 12

Solvent Injection Rate Dependence, HOPC

The same SS column as the one used in the preceding example was used here to see the effect of the solvent injection rate on the separation performance. A solution (20.7 wt. %) of polystyrene (Mw: $2.5\times10^5$, Mn: $9.6\times10^4$) in THF was injected at 0.05 mL/min and, as soon as the polymer was detected, the injection was switched to the solvent THF at 0.05, 0.1, and 0.2 mL/min.

Figure 13:
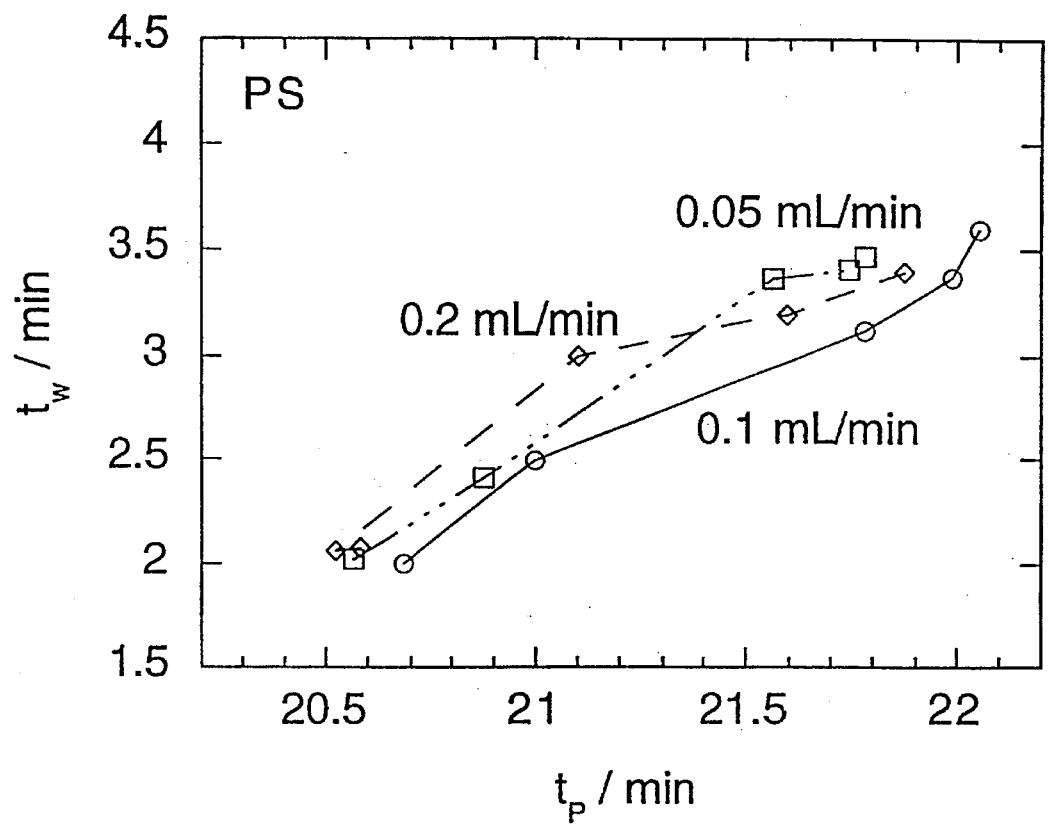

FIG. 13 shows the $t_w$-$t_p$ plot for the three solvent injection rates. The initial fractions show similar results as expected, but the later fractions' performance do depend on the solvent injection rate. The intermediate rate of 0.1 mL/min gives the optimal performance for the column used.

EXAMPLE 13

Pore Size Dependence, HOPC

Three SS columns of ID 3.9 mm and length 300 mm were used to see the effect of the pore size on the separation performance. Two of the columns were packed with silica gel (Davisil®) with bead size 37 μm and the pore sizes 6 and 15 nm. The third column as packed with silica gels purchased from Fluka with bead size 15 to 37 μm and a pore size 10 nm. A solution (20.7 wt. %) of polystyrene (Mw:

$2.5 \times 10^5$, Mn: $9.6 \times 10^4$) in THF was injected at 0.1 mL/min and, as soon as the polymer was detected, the injection was switched to the solvent THF at 0.1 mL/min.

Figure 14:
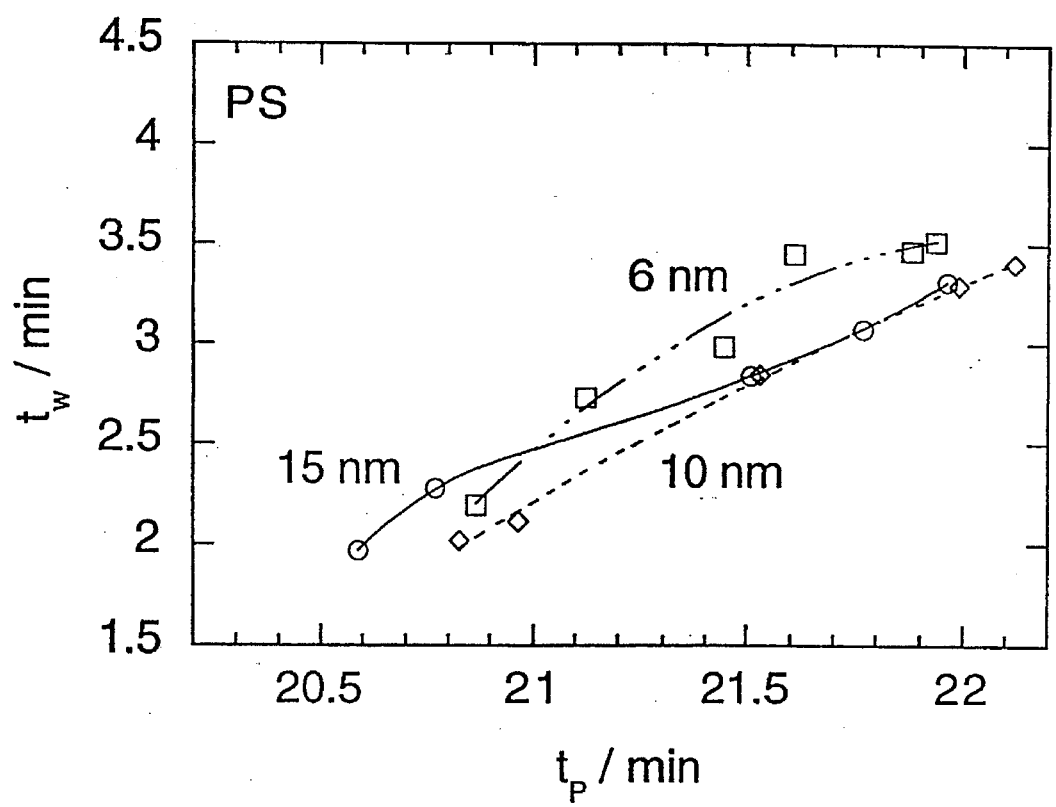

FIG. 14 shows the $t_w$-$t_p$ plot for the three pore sizes. The curve for 6 nm pore shows the worst performance, indicating that the pore channels were too narrow and therefore the diffusion coefficient of polymer was too much reduced to effectively partition polymers with respect to molecular weight at each plate at the given flow rate. The other two curves exhibit similar performance. The smaller pore size excels in separation of low molecular weight components, while the larger pore does well in the separation of the high molecular weight components.

EXAMPLE 14

Bead Size Dependence, HOPC

Three SS columns of ID 3.9 mm and length 300 mm were used to see the effect of the bead size on the separation performance. Two of the columns were packed with silica gel (Davisil®) with pore size 15 nm and bead sizes 18, 37, 52, and 100 μm. A solution (20.7 wt. %) of polystyrene (Mw: $2.5 \times 10^5$, Mn: $96 \times 10^4$) in THF was injected at 0.1 mL/min and, as soon as the polymer was detected, the injection was switched to the solvent THF at 0.1 mL/min.

Figure 15:
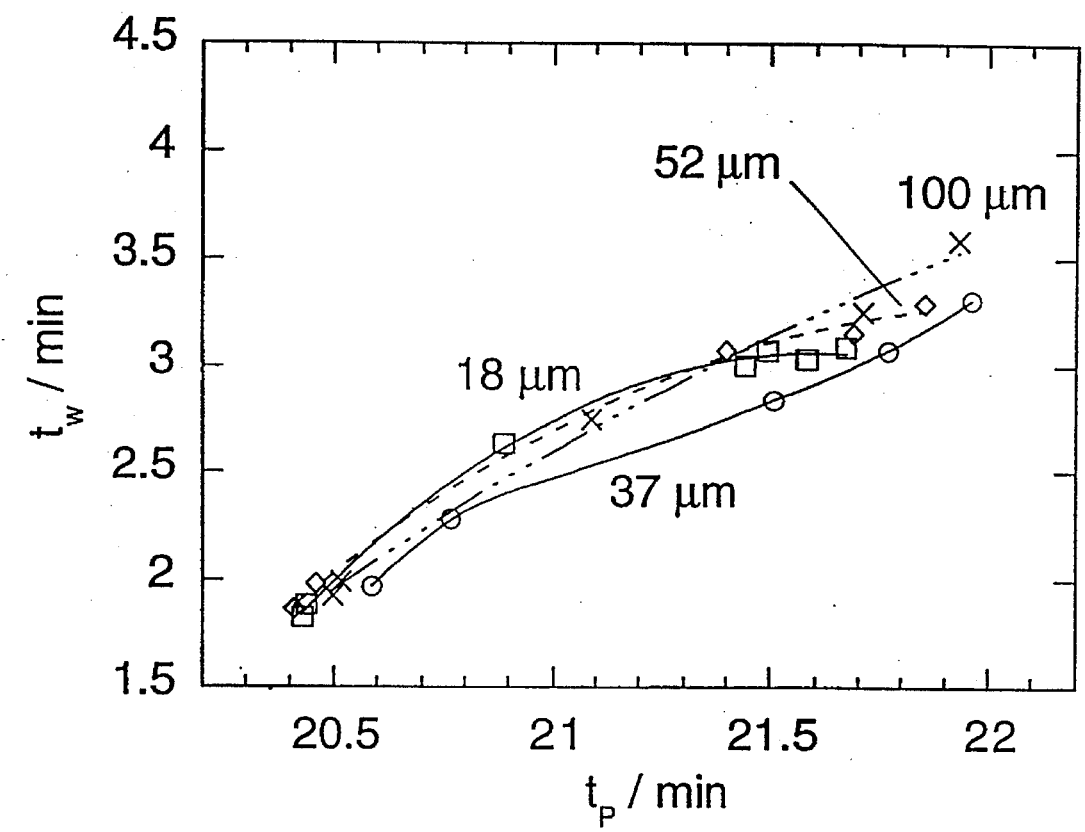

FIG. 15 shows the $t_w$-$t_p$ plot for the four bead sizes. Except for 37 μm bead, the performance is similar. The examples described thus far make clear that many parameters of HOPC can be varied by those skilled in the art for a given HOPC system.

EXAMPLE 15

EPF With Large Particles

About 3.2 g of treated porous glass beads (pore diameter 15 nm, bead size 2.3 mm, surface treated) were placed in a 20 mL scintillation vial. Excess solvent (toluene) was added to fill the pores. When the pores were filled, excess solvent was discarded.

About 3.1 g of semi-dilute solution of polymer (an equal-weight mixture of polystyrene standards of molecular weight of $3.0 \times 10^4$ and $2.9 \times 10^5$ in toluene, about 10 wt %) was introduced in the vial which was capped tightly. The vial was left on a rotation stage for equilibrium for about 11 days. The external solution was decanted into a nonsolvent (methanol) to precipitate the step 1 fraction. Excess solvent was added to the remaining porous glass beads to drive out the low molecular weight components from the pore channels. The vial was left on the rotation stage for equilibrium (about 10 days). The external solution was decanted into a nonsolvent (methanol) to precipitate the step 2 fraction. The porous glass beads were washed with solvent for regeneration and reprocessing.

Figure 16:
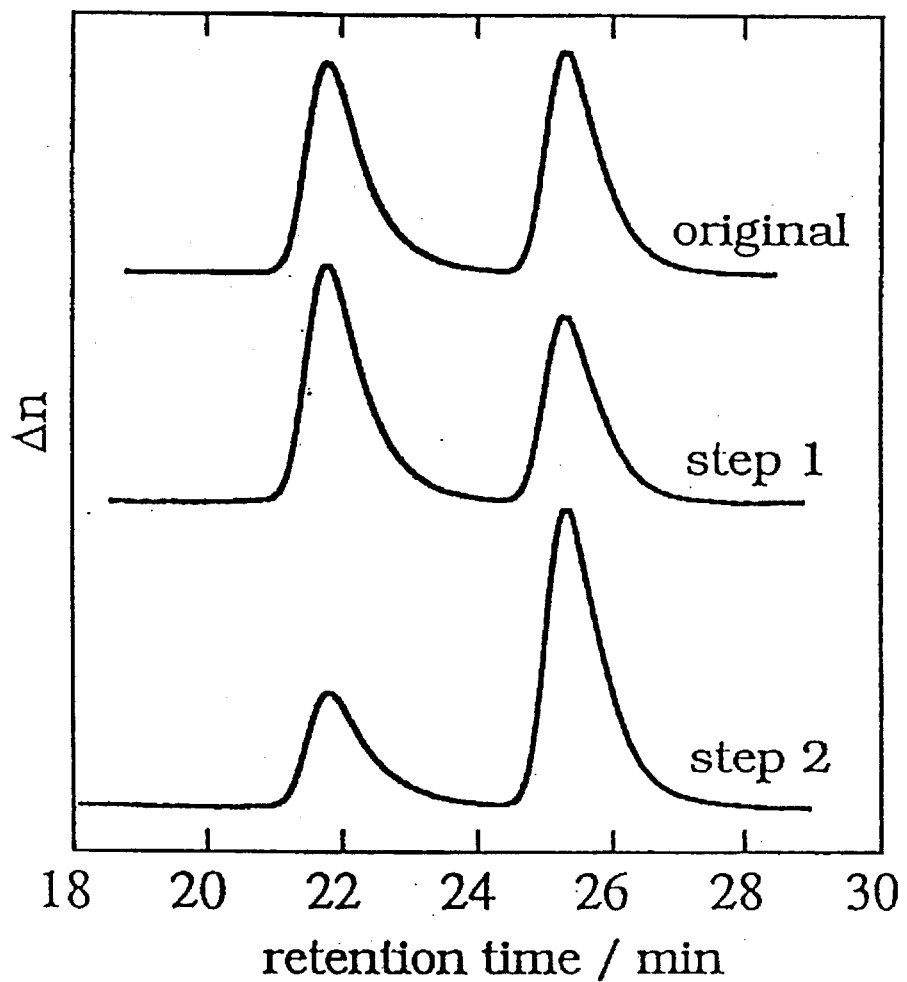
FIGS. 16–17 demonstrate the performance of EPF.

The molecular weight distributions for each of the enriched fractions (steps 1 and 2) and the original sample are shown in FIG. 16. Enrichment is evident.

EXAMPLE 16

EPF with Small Particles

Porous controlled pore glass was surface treated as previously described herein to prevent adsorption. A glass tubing (ID 13 mm, length 55 mm) was prepared. One of the openings was wrapped with a Teflon mesh (opening about 70 microns, thickness about 160 microns) to hold the porous materials in the tubing.

About one g of the treated controlled pore glass was placed in the teflon mesh-capped glass tubing. The tubing was placed in a shell vial.

Excess solvent was added (toluene) to fill the pore channels. Trapped air was removed at interstitial sites by placing the vial in a vacuum chamber. The inside tubing was taken out and exterior solvent was removed by blowing nitrogen into the open end of the tubing. The solvent in the shell vial was also discarded.

The tubing was returned into the shell vial and a semidilute solution of polymer in toluene was added into the tubing that holds solvent saturated porous materials. Air trapped at interstitial sites was again removed by placing the vial in a vacuum chamber. The shell vial was capped, placed on a rotation stage, and allowed to equilibrate for several days. The inside tubing was lifted and the exterior solution was expelled by blowing nitrogen into the open end tubing. The tubing was taken out.

The polymer was precipitated by adding nonsolvent (methanol) into the shell vial and recovering the product of stage 1.

The tubing was placed into another shell vial and excess solvent was added into the tubing. Air trapped at interstitial sites was removed by placing the vial in a vacuum chamber. The shell vial was capped, placed on a rotation stage, and allowed to equilibrate for several days. The inside tubing was lifted and the exterior solution expelled into the shell vial by blowing nitrogen into the open end of the tubing. The tubing was taken out. The polymer was precipitated by adding nonsolvent into the shell vial followed by recovering the stage 2 product. The porous materials in the tubing were washed several times with pure solvent for the next processing.

Figure 17:
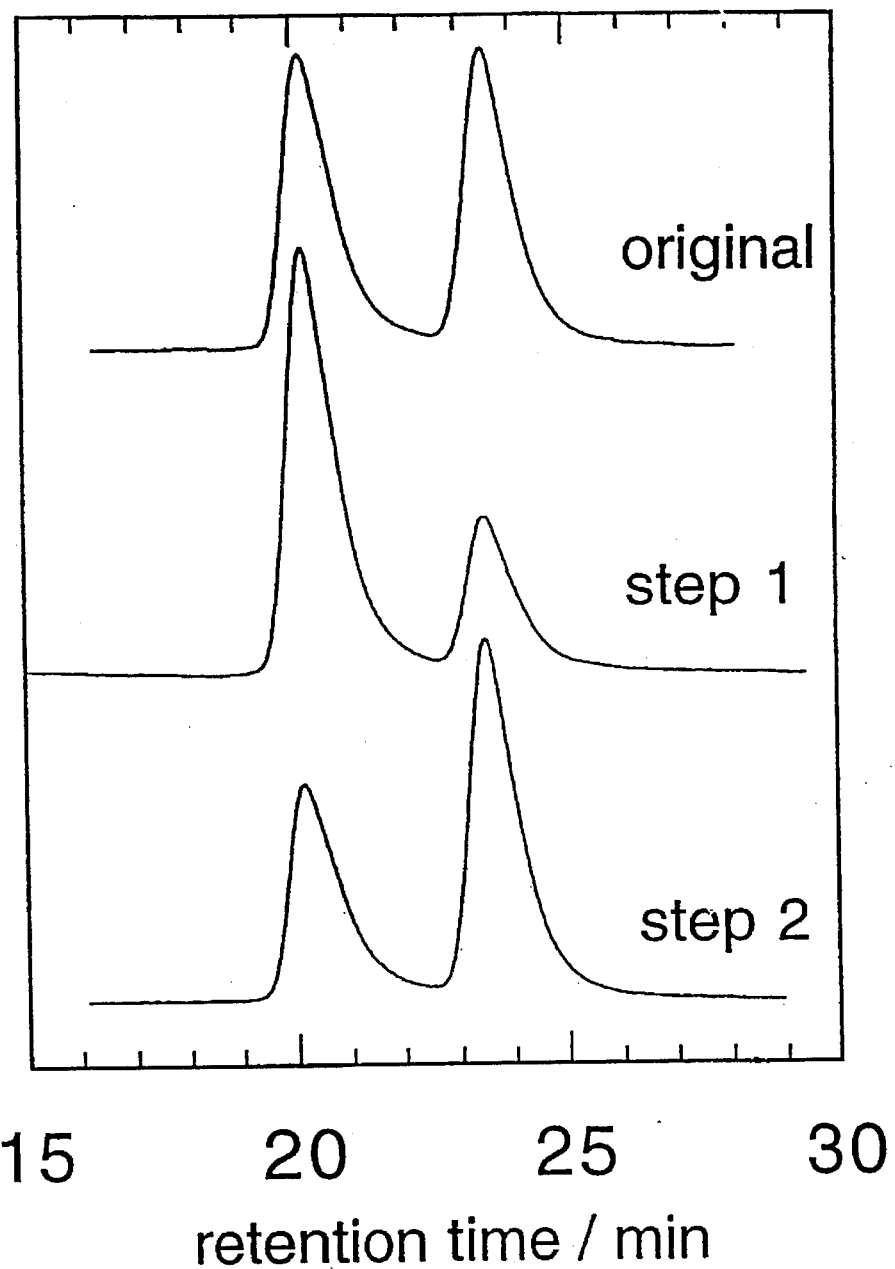

FIG. 17 shows further the performance of enhanced partitioning fractionation (EPF). EPF was applied to an equal weight mixture of two polystyrene fractions of molecular weight $9.0 \times 10^4$ and $9.5 \times 10^5$. 1.02 g of surface-treated controlled pore glasses of pore diameter 15 nm and the particle diameter around 150 μm (CPG, Inc.) were immersed into 1.06 g of a solution of the polymer mixture of 9.95 wt % in toluene. Six days were allowed to pass for the stage 1 to recover a fraction enriched with the high molecular weight component in the exterior solution. In stage 2 that drives a fraction enriched with the low molecular weight component out of the pore, two days were used. The result of the analytical GPC chromatograms for the stages 1 and 2 products and the original sample is shown in FIG. 17. The percentage of the high molecular weight component in stage 1 product is 72%, and that of low molecular weight component in stage 2 product is 62%. The recovered amount was 3 to 7 ratio. The enrichment effect by EPF is evident. Also, enrichment is clearly superior to that of FIG. 16.

EXAMPLE 17

EPF with Use of a Pump

The porous material was silane treated by the same procedure as described hereinabove. The column was packed with treated silica gel. A one-end capped glass or SS column is fixed to a vertical support. Fresh dried silica gel was poured through the top, open end of the column. The column was connected to a high-pressure liquid pump (SSI, AcuFlow Series II) through Teflon or SS tubing. Polar solvent such as cyclohexanone or THF was circulated through the column at high flow rate.

Cyclohexanone is nearly isorefractive with silica. When the air was removed, the column was nearly transparent.

When a space was created over the packed bed of silica in the column, the top fitting was removed and dried silica was added. The fitting was reconnected to the top fitting and more solvent was circulated. This was repeated until no space was left on the column.

A semidilute solution of the polymer in cyclohexanone was introduced through a four port valve until the front end of the solution reached the column outlet. The four port valve was turned to circulation mode. Time was taken for equilibrium between the mobile phase and all of the porous material.

The valve was turned back to the injection mode to inject pure solvent. The elution was collected from the column outlet and a fraction enriched in higher molecular weight products was recovered.

The valve was turned again to the circulation mode with excess amount of solvent in the vial, and equilibration between the mobile phase and the porous material was approached..

The valve was turned again to the injection mode and the exterior solution was replaced with pure solvent. The eluent was collected from the column outlet and a fraction enriched in low molecular weight components was recovered.

The column was washed by circulating pure solvent through the column for further processing.

While the invention has been described in detail and with reference to specific embodiments thereof, it will be apparent to one of ordinary skill in the art that various changes and modifications can be made therein without departing from the spirit and scope thereof.

What is claimed is:

1. A method for fractionating polymers based on molecular size comprising the steps of:
   (A) providing a solution of polymer dissolved in a first solvent, said polymer having an initial polydispersity index greater than 1.000 and including higher and lower molecular weight polymer components, said polymer being dissolved in said first solvent at a concentration about equal to or greater than an overlap concentration, c*, of said polymer but less than a concentration at which said solution is no longer fluid,
   (B) passing said solution as a mobile phase through a chromatographic matrix to generate an eluent, said matrix including a porous material imbibed with a second solvent, said second solvent imbibed in said porous material acting as a stationary phase in communication with said mobile phase, said porous material having pore openings of a dimension on the order of a molecular size of said polymer that allows said lower and higher molecular weight polymer components to migrate selectively between said mobile phase and said stationary phase to effect size-based partitioning of said polymer, whereby said migration is enhanced by a relatively high osmotic pressure generated because said concentration is about equal to or greater than said overlap concentration, c*, and
   (C) eluting said polymer from said porous material.

2. A method according to claim 1, further comprising the step of fractionating said eluent into a series of fractions, wherein each said fraction contains fractionated polymer having a polydispersity index less than said initial polydispersity index.

3. A method according to claim 2, wherein at least a portion of said fractionated polymer having a polydispersity index less than said initial polydispersity index is isolated from at least one of said fraction.

4. A method according to claim 1, wherein said concentration of said polymer component is equal to or greater than about twice said overlap concentration.

5. A method according to claim 1, wherein said concentration of said polymer component is equal to or greater than about thrice said overlap concentration.

6. A method according to claim 1, wherein said porous material comprises a porous inorganic material.

7. A method according to claim 1, wherein said porous material comprises porous silica.

8. A method according to claim 1, further comprising the step of treating said porous material before said passing step to prevent adsorption of said polymer onto said porous material.

9. A method according to claim 1, wherein said porous material has pore openings having an average pore diameter between about 4–100 nm.

10. A method according to claim 9, wherein said pore openings have an average pore diameter between about 5–30 nm.

11. A method according to claim 1, wherein said polymer has a number average molecular weight greater than about 1,000 g/mol.

12. A method according to claim 11, wherein said polymer component has a number average molecular weight greater than about 10,000 g/mol.

13. A method according to claim 1, wherein said polymer is a synthetic organic, semiorganic, organometallic, or inorganic polymer.

14. A method according to claim 1, wherein said polymer is a synthetic organic polymer.

15. A method according to claim 1, wherein said polymer is a natural polymer.

16. A method according to claim 1, wherein about when said eluent begins to elute from said porous material, a third solvent is passed through said porous material.

17. A method according to claim 16, wherein said first, second, and third solvents are the same solvents.

18. A method according to claim 1, wherein after said eluting step (C), said eluent is again passed as a mobile through a chromatographic matrix.

19. A method for fractionating polymers based on molecular size comprising the steps of:
   (A) providing a solution of polymer dissolved in a first solvent, said polymer having an initial polydispersity index greater than 1.000 and including higher and lower molecular weight polymer components, said polymer being dissolved in said first solvent at a concentration about equal to or greater than an overlap concentration, c*, of said polymer but less than a concentration at which said solution is no longer fluid,
   (B) passing said solution as a mobile phase onto a porous chromatographic matrix imbibed with a second solvent acting as a stationary phase until at least 50% of said matrix is in contact with said solution,
   (C) eluting said mobile phase from said matrix.

20. A method according to claim 19, wherein said passing step (B) is effected until at least about 90% of said matrix is in contact with said solution.

21. A method according to claim 19, wherein said passing step (B) is effected until essentially all of said matrix is in contact with said solution.

* * * * *